United States Patent
Al-Jaroudi et al.

(10) Patent No.: US 9,481,693 B1
(45) Date of Patent: Nov. 1, 2016

(54) MIXED LIGAND GOLD(III) COMPLEXES AS ANTI-CANCER AGENTS

(71) Applicant: KING FAHD UNIVERSITY OF PETROLEUM AND MINERALS, Dhahran (SA)

(72) Inventors: Said Al-Jaroudi, Qatif-Qudaih (SA); Muhammad Altaf, Dhahran (SA); Abdulaziz Al-Saadi, Dhahran (SA); Anvarhusein Abdulkadir Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/850,063

(22) Filed: Sep. 10, 2015

(51) Int. Cl.
  *C07F 1/12* (2006.01)
  *A61K 31/28* (2006.01)
  *A61K 45/06* (2006.01)

(52) U.S. Cl.
  CPC ............. *C07F 1/12* (2013.01); *A61K 31/28* (2013.01); *A61K 45/06* (2013.01)

(58) Field of Classification Search
  CPC ....................................................... C07F 1/12
  See application file for complete search history.

(56) References Cited

FOREIGN PATENT DOCUMENTS

CN     101847328 A     9/2010

OTHER PUBLICATIONS

Ito et al. "Absorption Spectra and Circular Dichroisms of Metal Complexes. I. Platinum(II)-, Palladium(II)- and Gold(III)-Complexes Containing Optically Active Diamines" Bulletin of the Chemical Society of Japan, 1967, pp. 2584-2891.*

R. Beklem Bostancioğlu, et al., "Investigation of the pharmacological profiles of dinuclear metal complexes as novel, potent and selective cytotoxic agents against *ras*-transformed cells", Environmental Toxicology and Pharmacology, vol. 37, No. 3, 2014, pp. 897-906.

John W. Williams, et al., "Dinuclear Platinum Complexes with Biological Relevance Based on the 1,2-Diaminocyclohexane Carrier Ligand", Inorganic Chemistry Communication, vol. 46, No. 15, 2007, pp. 5820-5822.

U.S. Appl. No. 14/798,071, filed Jul. 13, 2015, Al-Jaroudi, et al.

* cited by examiner

*Primary Examiner* — Joseph Kosack
(74) *Attorney, Agent, or Firm* — Oblon, McClelland, Maier & Neustadt, L.L.P.

(57) ABSTRACT

Gold(III) complexes with mixed ligands as anticancer agents. The gold(III) cations are coordinated to bidentate ligands having diamino functional groups: a diaminocyclohexane ligand and a 1,3-propylenediamine ligand. The diaminocyclohexane ligand can exist in both cis- and trans-configurations, resulting in isomeric gold(III) complexes. Also described are pharmaceutical compositions incorporating the gold(III) complexes, methods of synthesis, methods of treating cancer and methods of inhibiting cancer cell proliferation and inducing cancer cell apoptosis.

16 Claims, 20 Drawing Sheets

Cis

Trans

MIXED LIGAND GOLD(III) COMPLEXES AS ANTI-CANCER AGENTS

STATEMENT OF FUNDING ACKNOWLEDGEMENT

This project was funded by the National Plan for Science, Technology and Innovation (MAARIFAH)—King Abdulaziz City for Science and Technology—the Kingdom of Saudi Arabia, award number (14-MED64-04).

BACKGROUND OF THE INVENTION

1. Technical Field

The present invention relates to pharmaceutical compounds. More particularly, the present invention relates to gold(III) complexes having mixed diamine ligands. The present invention includes the use of these gold(III) complexes for treatment of cancers and cell proliferative disorders.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The development of new metal based therapeutic drugs with a pharmacological activity different from platinum drugs is one of the major goals of modern bioinorganic and bio-organometallic medicinal chemistry research [Bertrand B, Bodio E, Richard P, Picquet M, Gendre P L, Casini A (2015) J. Organomet. Chem. 775:124-129; Sadler P J, Sue R E (1994) Met. Based Drugs 1:107-144; Sava G, Bergamo A, Dyson P J (2011) Dalton Trans. 40:9069-9075; Shaw C F (1999) Chem. Rev. 99:2589-2600; Best S L and Sadler P J (1996) Gold Bull. 29:87-93; vanRijt S H and Sadler P J (2009) Drug Discov. Today 14(23-24):1089-1097; Panteli N, Stanojkovi T P, Zmejkovski B B, Sabo T J, Kaluderovic G N (2015) European Journal of Medicinal Chemistry 90:766-774; Al-Jaroudi S S, Fettouhi M, Wazeer M I M, Isab A A, Altuwaijri S (2013) Polyhedron 50:434-442—each incorporated herein by reference in their entirety]. The high effectiveness of cisplatin in the treatment of several types of tumors is severely hindered by some clinical problems such as normal tissue toxicity and the frequent occurrence of initial and acquired resistance to the drug [Kelland L (2007) Nat. Rev. Cancer 7:573-584; Thayer A M (2010) Eng. News 88:24-28; Dhar S, Lippard S J (2011) Bioinorg. MedChem, Wiley-VCH, Ch 3:79-96; Wang X, Guo X Z (2011) Bio-inorganic MediChem, Wiley-VCH, Ch 4:97-149—each incorporated herein by reference in its entirety]. Gold(III) complexes, which are isoelectronic and isostructural to platinum(II) complexes, show promising antitumor activity [Sadler P J (1976) Struct. Bond 29:171-214; Cutillas N, Yellol G S, de Haro C, Vicente C, Rodriguez V, Ruiz J (2013) Coord. Chem. Rev. 257:2784-2797—each incorporated herein by reference in their entirety]. Gold(III) complexes have recently gained considerable attention because they have strong antiproliferative effects and exhibited pharmacodynamics and kinetic properties that are different from cisplatin [Shaw C F (1999) Chem. Rev. 99:2589-2600—incorporated herein by reference in its entirety]. In general, gold(III) complexes are unstable under physiological conditions because they have a high reduction potential and hydrolyze fast. Therefore, selecting suitable ligands to enhance the stability of gold(III) complexes is a challenge.

In view of the foregoing, the present disclosure aims to provide stable gold(III) complexes having efficacy against a variety of cancers that also lack the severe toxic side effects associated with platinum-based drugs.

BRIEF SUMMARY OF THE INVENTION

According to a first aspect, the present disclosure relates to a gold(III) complex having Formula I:

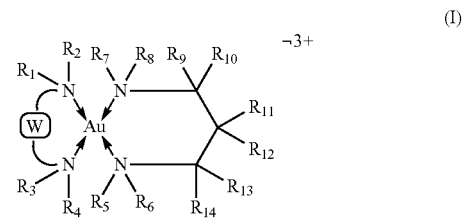

or a pharmaceutically acceptable salt, solvate, or prodrug thereof. The group, W, is selected from $W_1$ or $W_2$.

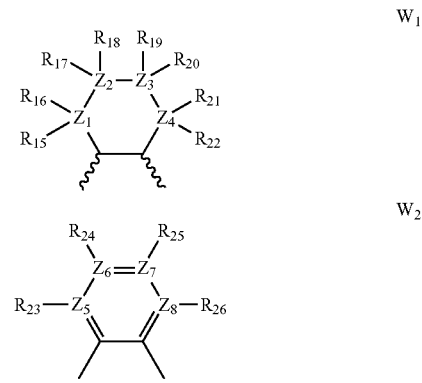

$R_1$-$R_8$ are each independently a hydrogen, an optionally substituted $C_1$-$C_8$ alkyl group, or an optionally substituted $C_6$-$C_8$ aryl group. $R_9$-$R_{14}$ are each independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group. $R_{15}$-$R_{26}$ are each independently a lone pair of electrons, a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group. $Z_1$-$Z_4$ are each independently a carbon, an oxygen, a sulfur, or a nitrogen atom. $Z_5$-$Z_8$ are each independently a carbon, or a nitrogen atom.

In some embodiments, the gold(III) complex has a formula selected from the group consisting of Formula II, Formula III, and Formula IV:

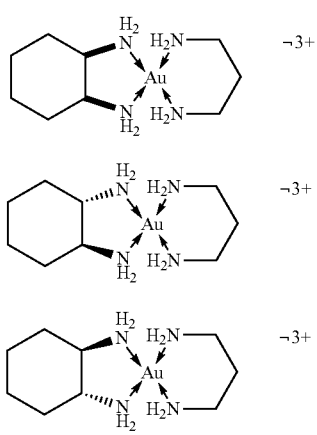

In at least one embodiment, the gold(III) complex is a pharmaceutically acceptable salt having one or more pharmaceutically acceptable anions selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

According to a second aspect, the present disclosure relates to a composition comprising the gold(III) complex or a pharmaceutically acceptable salt, solvate or prodrug thereof, and one or more pharmaceutically acceptable carriers.

In some embodiments, the composition further comprises one or more other active pharmaceutical agents.

In at least one embodiment, the composition has 50-99.9 wt % of the gold(III) complex relative to the total weight of the composition.

In some embodiments, the composition is in solid, semi-solid or liquid dosage forms.

In most embodiments, the composition is formulated for one or more modes of administration, including, oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration, and sublingual administration.

According to a third aspect, the present disclosure relates to a method for treating one or more types of cancer in a mammalian subject in need thereof, by administering a therapeutically effective amount of the composition of the second aspect to the mammalian subject.

In at least one embodiment, the gold(III) complex or a pharmaceutically acceptable salt, solvate or prodrug thereof, is administered in a dose of 0.05 mg/kg to 200 mg/kg based on the weight of the mammalian subject.

In some embodiments, the one or more types of cancer are prostate cancer and/or gastrointestinal cancer.

In at least one embodiment, the one or more types of cancer is resistant to cisplatin.

In at least one embodiment, the mammalian subject has renal disease.

According to a fourth aspect, the present disclosure relates to a method for inhibiting proliferation of cancer cells by contacting the cancer cells with the gold(III) complex or a pharmaceutically acceptable salt, solvate or prodrug thereof.

In some embodiments, the cancer cells are human cells.

In at least one embodiment, the cancer cells are prostate cancer cells and/or gastrointestinal cancer cells.

In some embodiments, the prostate cancer cells are PC3 cells, and the gastrointestinal cancer cells are SGC7901 cells.

In some embodiments, the gold(III) complex exhibits an $IC_{50}$ of 1-20 μM for inhibiting the proliferation of the cancer cells.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
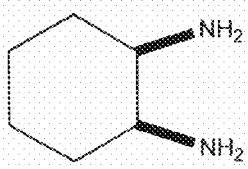
FIG. 1 shows the cis and trans isomers of diaminocyclohexane, a ligand used in one of the embodiments of the present disclosure.
Figure 1:
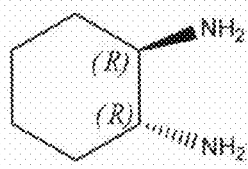
Figure 1:
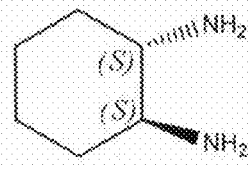

Embodiments of the present disclosure will now be described more fully hereinafter with reference to the accompanying drawings, in which some, but not all embodiments of the disclosure are shown.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically $C_1$ to $C_8$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term "optionally" includes substituted alkyl groups. Moieties with which the alkyl group can be substituted are selected from the group consisting of hydroxyl, amino, alkylamino, arylamino, alkoxy, thioalkoxy, aryloxy, nitro, cyano, sulfonate, sulfate, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonate, sulfate, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, "analog" refers to a chemical compound that is structurally similar to a parent compound, but differs slightly in composition (e.g., one atom or functional group is different, added, or removed). The analog may or may not have different chemical or physical properties than the original compound and may or may not have improved biological and/or chemical activity. For example, the analog may be more hydrophilic or it may have altered reactivity as compared to the parent compound. The analog may mimic the chemical and/or biologically activity of the parent compound (i.e., it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative," whereas the parent compound may not necessarily be used as the starting material to generate an "analog." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) *Curr. Pharm. Design.* 5(4):265-287; Pauletti et al. (1997). *Adv. Drug. Delivery Rev.* 27:235-256; Mizen et al. (1998) *Pharm. Biotech.* 11:345-365; Gaignault et al. (1996) *Pract. Med. Chem.* 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) *Eur. J. Drug Metab. Pharmacokinet.*, 15(2): 143-53; Balimane and Sinko (1999) *Adv. Drug Delivery Rev.*, 39(1-3):183-209; Browne (1997) *Clin. Neuropharmacol.* 20(1): 1-12; Bundgaard (1979) *Arch. Pharm. Chemi.* 86(1): 1-39; H. Bundgaard, ed. (1985) Design of Prodrugs, New York: Elsevier; Fleisher et al. (1996) *Adv. Drug Delivery Rev.* 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS PharmSci.*, 2(1): E6; Sadzuka Y. (2000) *Curr. Drug Metab.*, 1(1):31-48; D. M. Lambert (2000) *Eur. J. Pharm. Sci.*, 11 Suppl 2:S15-27—each incorporated herein by reference in its entirety]. In some embodiments, "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells.

In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The phrase "pharmaceutically acceptable" is employed herein to refer to counter-anions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the pharmaceutical composition refers to the combination of an active agent with a carrier, inert or active, making the composition especially suitable for diagnostic or therapeutic use in vivo or ex vivo.

"Pharmaceutically acceptable salt" refers to a gold(III) complex with a counter-anion. As used herein, the term "counter-anion" refers to an anion, preferably a pharmaceutically acceptable anion that is associated with a positively charged gold(III) complex of at least one of the Formulae I, II, III, and IV. Non-limiting examples of pharmaceutically acceptable counter-anions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetylacetonate. In some embodiments, the counter-anion is a halide, preferably chloride.

A "pharmaceutical composition" refers to a mixture of the compounds described herein or pharmaceutically acceptable salts, or prodrugs thereof, with other chemical components, such as physiologically acceptable carriers and excipients. One purpose of a pharmaceutical composition is to facilitate administration of at least one gold(III) complex to a subject.

As used herein, a "pharmaceutically acceptable carrier" refers to a carrier or diluent that does not cause significant irritation to an organism, does not abrogate the biological activity and properties of the administered gold(III) complex, and/or does not interact in a deleterious manner with the other components of the gold(III) complexes or the pharmaceutical composition in which it is contained. The term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol (2) proteins such as gelatin and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The terms "including", "such as", "for example" and the like are intended to refer to exemplary embodiments and not to limit the scope of the present disclosure.

Gold(III) Complexes and Pharmaceutical Compositions Thereof

The present disclosure provides gold(III) complexes having medicinal or pharmaceutical properties, preferably antitumor, anticancer and/or antiproliferative properties. In these gold(III) complexes, each central gold(III) atom is coordinated, preferably chelated by a first ligand and a second ligand. The first and second ligands can have either the same or different carbon skeleton. Preferably, the first and second ligands are diamines that utilize both amino functional groups to bind to the central gold(III) atom in a bidentate manner. The nitrogen atoms in the amino groups act as electron donors, which bind datively to the gold(III) atom.

One aspect of the disclosure relates to a gold(III) complex having Formula I:

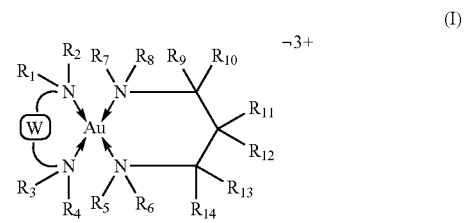

or a pharmaceutically acceptable salt, solvate, or prodrug thereof. The group, W, is selected from $W_1$ or $W_2$.

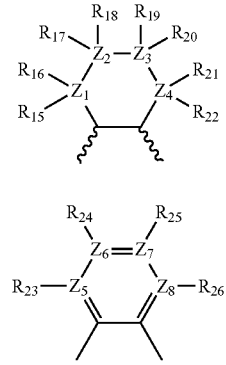

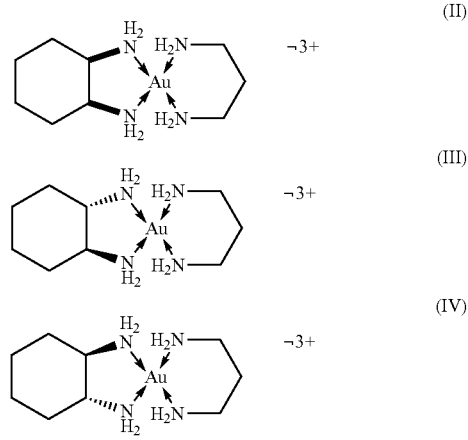

$R_1$-$R_8$ are each independently a hydrogen, an optionally substituted $C_1$-$C_8$ alkyl group, or an optionally substituted $C_6$-$C_8$ aryl group. $R_9$-$R_{14}$ are each independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group. $R_{15}$-$R_{26}$ are each independently a lone pair of electrons, a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group. $Z_1$-$Z_4$ are each independently a carbon, an oxygen, a sulfur, or a nitrogen atom. $Z_5$-$Z_8$ are each independently a carbon, or a nitrogen atom.

In a preferred embodiment, the ligands are diaminocyclohexane and propylenediamine, and their chemical structures are shown below:

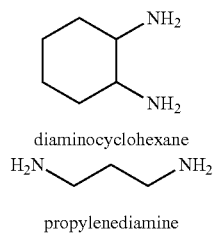

Diaminocyclohexane has two stereogenic carbon atoms, giving rise to cis and trans isomers of diaminocyclohexane (FIG. 1). These isomers bind to the gold(III) atom to yield gold(III) complexes with a formula selected from Formula II, Formula III, and Formula IV, where the gold(III) atom is coordinated to two donor nitrogen atoms from one diaminocyclohexane ligand and two donor nitrogen atoms from one propylenediamine ligand:

The generally accepted convention for representing stereochemical compounds, which is also adhered to herein, is the following:

a compound represented without stereo bonds, e.g. fragment $W_1$, is racemic or the configuration of the stereogenic center(s) is not defined;

a compound described with one of the descriptors "(±)", "rel", or "rac", is racemic;

a compound represented with solid bars, e.g. Formula II, refers to a non-racemic compound and the stereochemistry of the stereogenic centers are relative;

a compound represented with solid and broken wedges, e.g. Formulae III and IV, but without the descriptors "(±)", "rel", or "rac" refers to a non-racemic or an enantio-enriched compound, where its stereochemistry is absolute.

Another aspect of the present disclosure relates to a pharmaceutical composition comprising one or more of the gold(III) complexes described herein. In one embodiment, the compositions include a therapeutically effective amount of one or more of the gold(III) complexes described herein or derivatives thereof in combination with a pharmaceutically acceptable carrier and, in addition, may include other medicinal agents, pharmaceutical agents, carriers, diluents or other non-active ingredients. In one embodiment, the pharmaceutically acceptable carrier comprises a binder. In at least one embodiment, the composition has 50-99.9 wt % of the gold(III) complexes relative to the total weight of the composition, preferably 60-99.9 wt %, preferably 70-99.9 wt %, preferably 80-99.9 wt %, more preferably 90-99.9 wt %. The amount of active ingredients that can be combined with the carrier materials to produce a single dosage form varies depending upon the mammalian subject treated and the particular mode of administration.

In certain embodiments, a gold(III) complex of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab, and the like.

In treating certain cancers, the best approach is a combination of surgery, radiotherapy, and/or chemotherapy. Therefore, in at least one embodiment, the pharmaceutical composition is employed with radiotherapy. In another embodiment, the pharmaceutical composition is employed with surgery.

Depending on the intended mode of administration (oral, parenteral, or topical), the pharmaceutical composition can be in the form of solid, semi-solid or liquid dosage forms, such as tablets, suppositories, pills, capsules, powders, liquids, or suspensions, preferably in unit dosage form suitable for single administration of a precise dosage.

In a preferred embodiment, the pharmaceutical composition is administered orally. Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, an analog or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The gold(III) complexes, or their analogs or derivatives of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analog or derivative thereof can be prepared by mixing an analog or derivative thereof with a suitable nonirritating excipient such as cocoa butter, synthetic mono- di- or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

Methods of Treating Cancers and Combination Therapies

A mixed diamine ligand gold(III) complex of the present disclosure or an analog or derivative thereof may be used in conjunction with one or more additional compounds, in the treatment or prevention of neoplasm, of tumor or cancer cell division, growth, proliferation and/or metastasis in a mammalian subject; induction of death or apoptosis of tumor and/or cancer cells; and/or any other form of proliferative disorder. As used herein, "a subject in need thereof" refers to a mammalian subject, preferably a human subject, who has been diagnosed with, is suspected of having, is susceptible to, is genetically predisposed to or is at risk of having at least one form of cancer.

The neoplastic activity of the tumor or cancer cells may be localized or initiated in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system. In some embodiments, methods incorporating the use of at least one of the gold(III) complexes of the present disclosure are effective in the treatment or prevention of cancer of the aforementioned locations.

The mixed diamine ligand gold(III) complex of the present disclosure or the pharmaceutical composition thereof is especially effective in the treatment or prevention of prostate cancer and/or gastrointestinal cancer.

In addition, gold(III) complexes have been reported to be effective against cisplatin resistant cancers because these complexes may have a different mechanism of action [Ronconi L, Aldinucci D, Dou Q P D (2010) Anticancer Agents Med. Chem. 10:283-292; To Y F, Sun R W Y, Chen V S F, Chan W Y, Yu P K H, Tam C M, Che C, Lin L S (2009) Int. J. Cancer 124:1971-1979—each incorporated herein by reference in its entirety]. In some embodiments, the gold(III) complexes described herein are used to treat cancers that are resistant to cisplatin. Resistance to cisplatin may be substantially greater, as shown in studies with tumor cell lines established from clinically refractory tumors, which require cytotoxic concentrations as much as 50-100-fold in excess of those needed for sensitive tumor cells [Hills C A, Kelland L R, Abel G, Siracky J, Wilson A P and Harrap K R. (1989). Br. J. Cancer 59:527-534—incorporated herein by reference in its entirety]. These cisplatin-resistant cells have mechanisms to prevent cisplatin from interacting with cellular DNA, and/or interfere with the DNA damage signals from activating the cell death mechanism [Henkels K M and Turchi J J. (1999). Cancer Res. 59:3077-3083—incorporated herein by reference in its entirety].

Cattaruzza et al. reported gold(III) complexes having lower nephrotoxicity [Cattaruzza L, Fregona D, Mongiat M, Ronconi M, Fassina A, Colombatti A, Aldinucci D (2010) Int. J. Cancer 128(1):206-215—incorporated herein by reference in its entirety]. Thus, in at least one embodiment, the gold(III) complexes are used to treat cancer patients inflicted with renal disease. Examples of renal disease include, autosomal dominant polycystic kidney disease, autosomal recessive polycystic kidney disease, acute pre-renal kidney failure, acute intrinsic kidney failure, chronic pre-renal kidney failure, chronic intrinsic kidney failure, chronic post-renal kidney failure.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more gold(III) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, after treatment with the one or more gold(III) complexes of a pharmaceutical composition thereof, the size of a tumor does not reduce but is maintained the same as the tumor size before treatment. Methods of assessing tumor size include but are not limited to CT scan, MRI, DCE-MRI and PET scan.

In some embodiments, the method for treating cancer and other proliferative disorders involves the administration of a unit dosage or a therapeutically effective amount of one or more of gold(III) complexes or a pharmaceutical composition thereof to a mammalian subject (preferably a human subject) in need thereof. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. In at least one embodiment, the pharmaceutical composition is administered in a dose of 0.05-200 mg/kg based on the weight of the mammalian subject, preferably 10-150 mg/kg, more preferably 50-100 mg/kg. The one or more of gold(III) complexes or a pharmaceutical composition thereof may be administered in a single dose or multiple individual divided doses. In some embodiments, the interval of time between the administration of gold(III) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, mixed diamine ligand gold(III) compounds and one or more additional therapies are administered less than 1 day, 1 week, 2 weeks, 3 weeks, 4 weeks, one month, 2 months, 3 months, 6 months, 1 year, 2 years, or 5 years apart.

Method of Inhibiting Proliferation of Cancer Cells and Inducing Cancer Cell Death The present disclosure further provides a method of inhibiting proliferation of human cancer cells and inducing apoptosis of the human cancer cells in vitro or in vivo. Human cancer cells are contacted with 1-100 µM of a gold(III) complex in accordance with the present disclosure or a composition comprising the gold(III) complex at the defined concentration range, preferably 2-75 µM, more preferably 5-50 µM, even more preferably 5-15 µM. The viability of cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay, Trypan Blue assay and TUNEL assay. In a preferred embodiment, a MTT assay is used.

When contacted with one or more of the gold(III) complexes at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

In at least one embodiment, the human cancer cells are derived from commercial cell lines, including but are not limited to HeLa cervical cancer cells, A549 lung cancer cells, HCT-15 colon cancer cells, HCT-8 or HRT-8 colon cancer cells, DLD-1 colon cancer cells, MCF-7 breast cancer cells, A2780 ovarian cancer cells, and DU-145 prostatic cancer cells. In a preferred embodiment, SGC7901 gastrointestinal and PC3 prostate cancer cells are used. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis cisplatin-resistant ovarian cancer cells and SGC7901-cis cisplatin-resistant gastrointestinal cancer cells. In other embodiments, the human cancer cells are cancer cells of a human patient who has been diagnosed with, is suspected of having, or is susceptible to or at risk of having at least one form of cancer, preferably prostate cancer and/or gastrointestinal cancer.

The half maximal inhibitory concentration ($IC_{50}$) values of the gold(III) complexes against the human cancer cells are no higher than 100 µM, preferably at least no higher than 50 μM, more preferably no higher than 30 μM, no higher than 20 μM, even more preferably no higher than 12 μM. In some embodiments, the $IC_{50}$ value of the gold (III) complexes against human prostate or gastrointestinal cancer cells, such as but not limited PC3 and SGC7901 cell lines, are ranged 1-20 μM, preferably 2-15 μM, more preferably 3-12 μM, even more preferably 4-12 μM.

EXAMPLES

The following examples have been included to further describe protocols for synthesizing and characterizing certain mixed diamine ligand gold(III) complexes (i.e. propylenediamine and diaminocyclohexane ligands), and results thereof. It should be noted that these examples have been included for illustrative purposes, and are not intended to limit the scope of the appended claims.

Example 1

Synthesis of Gold(III) Complexes

Sodium tetrachloroaurate(III) dihydrate $NaAuCl_4 \cdot 2H_2O$ and 1,3-propylenediamine (pn) were purchased from Sigma-Aldrich. Ligands, cis-1,2-diaminocyclohexane (cis-DACH), trans-(±)-1,2-diaminocyclohexane (trans-(±)-DACH) and (S,S)-(+)-diaminocyclohexane ((S,S)-DACH) were purchased from Aldrich. Absolute $C_2H_5OH$, $CH_3OH$, $D_2O$ and DMSO-$d_6$ were obtained from Fluka Chemicals Co. All other reagents as well as solvents were obtained from Aldrich Chemical Co., and used as received.

Mixed ligand gold(III) chloride compounds, cis-1,2-diaminocyclohexane(1,3-propylenediamine)gold(III) chloride, [(pn)Au{cis-(1,2-DACH)}]$Cl_3$ 1, trans-(±)-1,2-diaminocyclohexane(1,3-propylenediamine)gold(III) chloride, [(pn)Au{(trans-(±)-(1,2-DACH)}]$Cl_3$ 2, and (S,S)-(+)-1,2-diaminocyclohexane(1,3-propylenediamine)gold (III) chloride [(pn)Au{(S,S)-(+)-(1,2-DACH)}]$Cl_3$ 3, were synthesized using one mole of sodium tetrachloroaurate(III) dihydrate $NaAuCl_4 \cdot 2H_2O$ with one mole of 1,3-propylenediamine (pn) and one mole of cis-DACH or trans-(±)-DACH or (S,S)-(+)-DACH respectively according to a previously reported procedure [Al-Jaroudi S S, Monim-ul-Mehboob M, Altaf M, Al-Saadi A A, Wazeer M I M, Altuwaijri S, Isab A A (2014) Biometals (2014) 27:1115-1136—incorporated herein by reference in its entirety].

Sodium tetrachloroaurate dihydrate, $NaAuCl_4 \cdot 2H_2O$, 398 mg (1.0 mmol) was dissolved in a minimum volume of absolute ethanol (10 ml) at ambient temperature. In a separate beaker, 1,2-diaminocyclohexane (1,2-DACH), 114 mg (1.0 mmol) was dissolved in a minimum volume of absolute ethanol (10 ml) at ambient temperature. Both solutions were mixed dropwise and stirred for a half hour. Finally, a clear solution was obtained and filtered. In a separate beaker, 1,3-propylenediamine (pn), 74 mg (1.0 mmol) is dissolved in a minimum volume of absolute ethanol (10 ml) at ambient temperature. The pn solution is added dropwise to the above filtered solution. Upon stirring overnight, the white precipitate of [(pn)Au(1,2-DACH)]$Cl_3$ was obtained. The product was isolated, dissolved in 2 mL of water and filtered through celite pad to remove NaCl. Addition of 100 mL of cold $CH_3OH$ to the filtrate and a white precipitate was obtained filtered and washed with cold $CH_3OH$. The solid product was dried under reduced pressure with $P_2O_5$. The yield of the compounds 1, 2 and 3 was in the range of 70-73%. Melting points and elemental analysis for complexes are presented in Table 1.

TABLE 1

Melting point (MP) and CHN analysis of gold(III) complexes 1, 2 and 3.

| Complex | Melting point (° C.) | Found(Calc.)% | | |
|---|---|---|---|---|
| | | H | C | N |
| (1).3H$_2$O | 161-163 | 5.57(5.54) | 19.64(19.81) | 10.25(10.27) |
| (2).3H$_2$O | 171-173 | 5.59(5.54) | 19.67(19.81) | 10.21(10.27) |
| (3).3H$_2$O | 173-175 | 5.52(5.54) | 19.74(19.81) | 10.24(10.27) |

Example 2

Electronic Spectra

Electronic spectra were obtained for the gold(III) complexes using the Lambda 200, Perkin-Elmer UV-Vis spectrometer. UV-Vis spectroscopy was used to determine the stability of the complexes in a physiological buffer (40 mM phosphate, 4 mM NaCl, pH 7.4). Electronic spectra were recorded on freshly prepared of each complex in buffer solution at room temperature. Then, their electronic spectra were monitored over 3 days at 37° C. The UV-Vis absorption data is shown in Table 2.

TABLE 2

$\lambda_{max}$ values derived from UV-Vis spectra for gold(III) complexes 1, 2 and 3.

| Complex | $\lambda_{max}$ (nm) |
|---|---|
| NaAuCl$_4$ | 293 |
| 1 | 332 |
| 2 | 339 |
| 3 | 341 |

The gold(III) complexes 1, 2 and 3 dissolved in a reference buffered phosphate solution exhibit intense absorptions in the range 332-341 nm, which are assigned to ligand-to-metal charge-transfer (LMCT) transitions characteristically associated to the gold(III) center [Esumi K, Nawa M, Aihara N, Usui K (1998) New J. Chem. 20:719-720—incorporated herein by reference in its entirety]. These absorption bands were previously assigned to $NH^-$—Au(III) charge-transfer bands. It is worth-mentioning that these spectral features appear only at relatively high pH values (pH>6-7) at which the deprotonation of ligand has fully occurred. According to crystal field theory for $d^8$ complexes the lowest unoccupied molecular orbital (LUMO) orbital is $d_{x^2-y^2}$, so ligand to metal charge transfer could be due to $p_\sigma \rightarrow d_{x^2-y^2}$ transition [Haruko I, Junnosuke F, Kazuo S (1967) Bull. Chem. Soc. Jpn. 40:2584-2591—incorporated herein by reference in its entirety]. Additionally, there was no absorption observed at around 293 nm which corresponds to the charge transfer of the counter ion chloride to gold(III), indicating the absence of the dichlorido(1,2-DACH)gold(III) chloride complex.

Figure 12A:
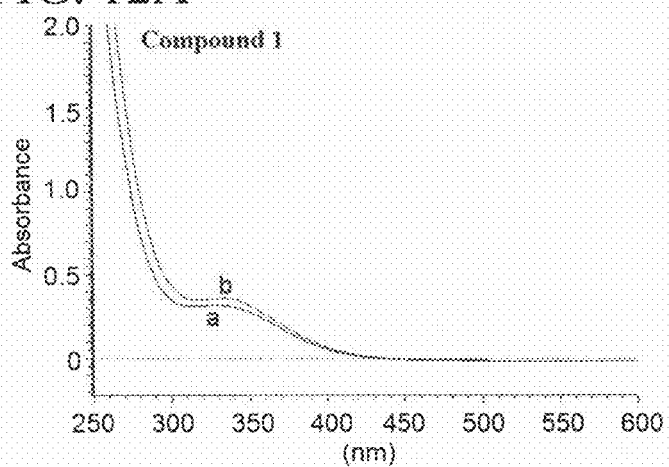
FIG. 12A shows the UV-Vis spectra of complex 1 dissolved in the buffer solution at 37° C. (a) just after mixing, and (b) after 3 days.
Figure 12B:
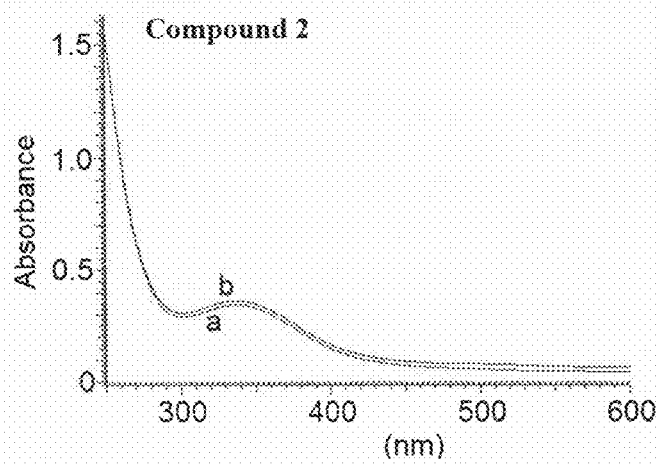
FIG. 12B shows the UV-Vis spectra of complex 2 dissolved in the buffer solution at 37° C. (a) just after mixing, and (b) after 3 days.
Figure 12C:
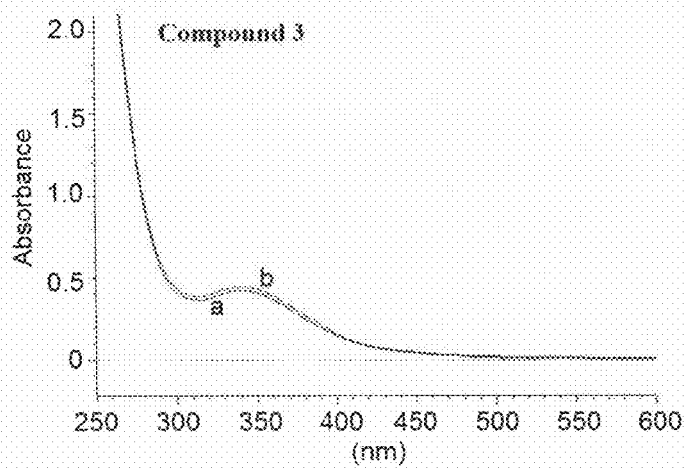
FIG. 12C shows the UV-Vis spectra of complex 3 dissolved in the buffer solution at 37° C. (a) just after mixing, and (b) after 3 days.

The electronic spectra of compounds 1, 2 and 3 were monitored at 37° C. over 3 days after mixing in the buffer solution. The electronic spectra for compounds 1, 2 and 3 immediately after mixing and after 3 days are illustrated in FIGS. 12A to 12C. It is apparently observed that the transitions remain relatively unmodified over a period of 3 days. Such observations show a substantial evidence for the stability of these compounds 1, 2 and 3 under the conditions of solution state. Nevertheless, a slight decrease in intensity of the characteristic bands was noticed with time without significant modifications in shape of spectra. Further, such observation indicates that the gold center in these compounds remains in the +3 oxidation state. The minor spectral changes that are generally observed within the first hours may be ascribed either to dissociation of the amine ligands from the gold(III) complex or to partial reduction of gold (III) to metallic gold. In general, however, loss of spectral intensity is lower than 10% of the original intensity within the observation period of 3 days which indicates high stability of these compounds in the buffer.

It is possible that compounds 1, 2 and 3 would be stable enough in the physiological environment to undergo the necessary reactions/interactions required for bioactivity.

Example 3

Mid and Far-IR Studies

The IR spectra of the ligands and their gold(III) complexes were recorded on a Perkin-Elmer FT-IR 180 spectrophotometer using KBr pellets over the range 4000-400 $cm^{-1}$. The selected IR frequencies are given in Table 3.

ligands. This is most likely due to stronger H-bonding interactions in the free ligands compared to the two coordinated amino groups of DACH, leading to formation of five-membered ring with the gold(III) atom in compounds 1 to 3. The coordination of the nitrogen atom with the gold(III) atom, and the formation of Au—N bond can be supported by the presence of a ν(Au—N) band at 425-451 $cm^{-1}$ in the far-IR [Arsenijevic M, Milovanovic M, Volarevic V, Djekovic A, Kanjevac T, Tatjana A, Nebojsa D, Svetlana D, Bugarcic Z (2012) Med. Chem. 8:2-8. Becke A D (1988) Phys. Rev. 38:3098—incorporated herein by reference in its entirety]. The C—N stretching bands also showed a significant shift to higher wavenumber, indicating a shorter C—N bond in the compound than in the free ligand. Moreover, there was no signal observed at 352 and 367 $cm^1$ corresponding to the symmetric and asymmetric stretching of the Cl—Au—Cl bonds in [(1,2-DACH)AuCl$_2$]$^+$ complexes (Al-Jaroudi S S et al. (2013) Polyhedron 50:434-442—incorporated herein by reference in its entirety). The [{(1,2-DACH)}Au(pn)]Cl$_3$ complexes 1 to 3 show N—H

TABLE 3

IR frequencies, ν($cm^{-1}$) for cyclohexanediamine-gold(III)-propylenediamine complexes.

| Complex | ν(N—H) | ν$_{shift}$ | ν(C—N) | ν$_{shift}$ | Refs. |
|---|---|---|---|---|---|
| pn | 3357 m, 3282 m | | 1093 w | | d |
| (pn)AuCl$_3$ | 3447 br | 127 | 1178 s | 85 | d |
| cis-1,2-(DACH) | 3356 m, 3286 m | | 1092s | | e |
| [cis-1,2-(DACH)AuCl$_2$]Cl | 3414 w | 93 | 1183 s | 91 | e |
| 1 | 3426br, 3106 br | 105$^a$, 107$^b$ | 1163w | 71$^a$, 70$^b$ | c |
| trans-(±)-1,2-(DACH) | 3348 m, 3271 m, 3183 m | | 1082 m | | e |
| [trans-(±)-1,2-(DACH)AuCl$_2$]Cl | 3485 w, 3420 w, 3384 w | 137, 149, 201 | 1175 m | 93 | e |
| 2 | 3452br, 3112 br | 131$^a$, 133$^b$ | 1184 m | 92$^a$, 91$^b$ | c |
| (S,S)-(+)-1,2-(DACH) | 3340 m, 3252 m, 3167 m | | 1082 m | | e |
| [(S,S)-(+)-1,2-(DACH)AuCl$_2$]Cl | 3604 m, 3340 m, 3306 m, 3168 m | 132, 27 | 1171 m | 89 | e |
| 3 | 3444br, 3118 | 123$^a$, 125$^b$ | 1186 m | 94$^a$, 93$^b$ | c |

$^a$with respect to DACH,
$^b$with respect to pn,
$^c$this work,
$^d$Al-Maythalony BA et al. (2009) Inorg. Chim. Acta. 362:3109-3113 — incorporated herein by reference in its entirety,
$^e$Al-Jaroudi SS et al. (2013) Polyhedron 50:434-442 — incorporated herein by reference in its entirety.

Far-infrared spectra were recorded for complexes 1, 2 and 3 at 4 $cm^{-1}$ resolution at room temperature in cesium chloride disks on a Nicolet 6700 FT-IR with far-IR beam splitter. Far-IR data for the complexes are shown in Table 4.

TABLE 4

Far-IR frequencies, ν($cm^{-1}$) for 1, 2, and 3 complexes.

| Species | Au—Cl | Au—N | Refs. |
|---|---|---|---|
| NaAuCl$_4$ | 365 | — | a |
| [(pn)AuCl$_2$]Cl | — | 391,474 | b |
| [{cis-1,2-(DACH)}AuCl$_3$]Cl | 352, 367 | 437 | c |
| 1 | — | 331, 425 | a |
| [{trans-(±)-1,2-(DACH)}AuCl$_2$]Cl | 353, 365 | 437 | c |
| 2 | — | 392, 448 | a |
| [{(1S,2S)-(+)-(DACH)}AuCl$_2$]Cl | 353, 366 | 395, 436 | c |
| 3 | — | 383, 451 | a |

$^a$this work,
$^b$Al-Maythalony BA et al. (2009) Inorg. Chim. Acta. 362:3109-3113 — incorporated herein by reference in its entirety,
$^c$Al-Jaroudi SS et al. (2013) Polyhedron 50:434-442 — incorporated herein by reference in its entirety.

It is observed that N—H stretching vibrations of complexes 1-3 exhibit, in the range 3426-3452 $cm^{-1}$, a blue shift compared to the amino group of the corresponding free stretching frequencies generally lower in comparison with [{(1,2-DACH)}AuCl$_2$]Cl complexes (Table 3), most probably due to stronger hydrogen bonding interactions with the chloride anions in the [(DACH)Au(pn)]Cl$_3$ complexes. Furthermore the Au—N stretching frequencies are consistent with weaker Au—N bond strength in complexes 1 to 3 compared to [(1,2-DACH)AuCl$_2$]Cl complexes.

Example 4

Solution NMR Measurements

Figure 2A:
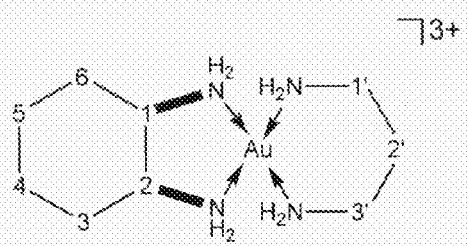
FIG. 2A shows the structure of complex 1.
Figure 2B:
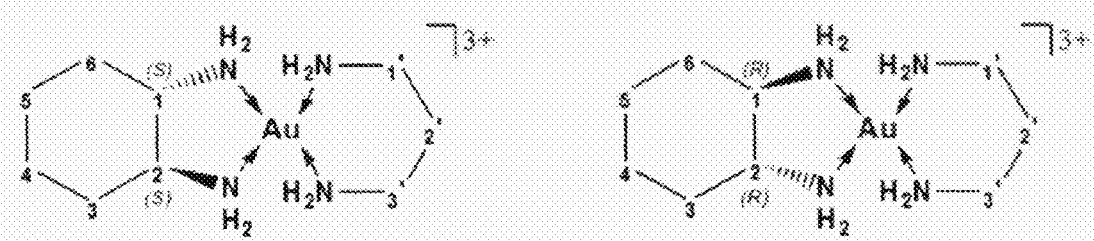
FIG. 2B shows the structure of complex 2 as a mixture of both enantiomeric forms.
Figure 2C:
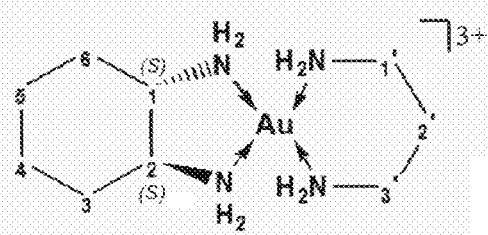
FIG. 2C shows the structure of complex 3.

All NMR measurements were carried out on a Jeol JNM-LA 500 NMR spectrophotometer at 297K. The $^1$H NMR spectra were recorded at a frequency of 500.00 MHz. The $^{13}$C NMR spectra were obtained at a frequency of 125.65 MHz with $^1$H broadband decoupling and referenced relative to TMS. The spectral conditions were: 32 k data points, 0.967 s acquisition time, 1.00 s pulse delay and 45 pulse angle. The chemical shifts are referenced to 1,4-dioxane as an internal standard. The $^1$H and $^{13}$C NMR chemical shifts are given in Table 5 and Table 6, respectively, according to FIGS. 2A, 2B, and 2C.

TABLE 5

$^1$H NMR chemical shifts of free ligands and cyclohexanediamine-Au(III)-propylenediamine complexes in D$_2$O.

| Compound | H1, H2 | H3, H6 (eq) | H3, H6 (ax) | H4, H5 (eq) | H4, H5 (ax) | H1', H3' | H2' | Ref. |
|---|---|---|---|---|---|---|---|---|
| pn | — | — | — | — | — | 2.98, t | 1.94, pt | a |
| cis-1,2-(DACH) | 2.23, m | 1.85, m | 1.69, m | 1.28, m | 1.12, m | — | — | b |
| trans-(±)-(DACH) | 2.25, m | 1.85, m | 1.68, m | 1.28, m | 1.11, m | — | — | b |
| (1S,2S)-(+)-1,2-(DACH) | 2.24, m | 1.85, m | 1.69, m | 1.28, m | 1.11, m | — | — | b |
| 1 | 3.65, m | 1.96, m | 1.79, m | 1.60, m | 1.41, m | 2.94, m | 2.19, m, 1.96, m | a |
| 2 | 3.07, m | 2.11, m | 1.56, m | 1.47, m | 1.10, m | 2.91, m | 2.12, m | a |
| 3 | 3.08, m | 2.11, m | 1.56, m | 1.47, m | 1.11, m | 2.91, m | 2.13, m | a |

$^a$this work,
$^b$Al-Jaroudi SS et al. (2013) Polyhedron 50: 434-442 - incorporated herein by reference in its entirety.

TABLE 6

$^{13}$C NMR chemical shifts of free ligands and cyclohexanediamine-gold(III)-propylenediamine complexes in D$_2$O.

| Compound | C1,C2 | C3,C6 | C4,C5 | C1',C3' | C2' |
|---|---|---|---|---|---|
| (pn) | — | — | — | 37.47 | 25.69 |
| cis-1,2-(DACH) | 58.20 | 35.26 | 26.36 | — | |
| trans-(±)-1,2-(DACH) | 58.46 | 35.55 | 26.63 | — | |
| (1S,2S)-(+)-1,2-(DACH) | 58.27 | 35.32 | 26.43 | — | |
| 1 | 61.98 | 26.92 | 20.73 | 40.95 | 26.92 |
| 2 | 64.47 | 32.88 | 23.91 | 40.90 | 26.90 |
| 3 | 64.50 | 32.90 | 23.94 | 40.92 | 26.92 |

Figure 13:
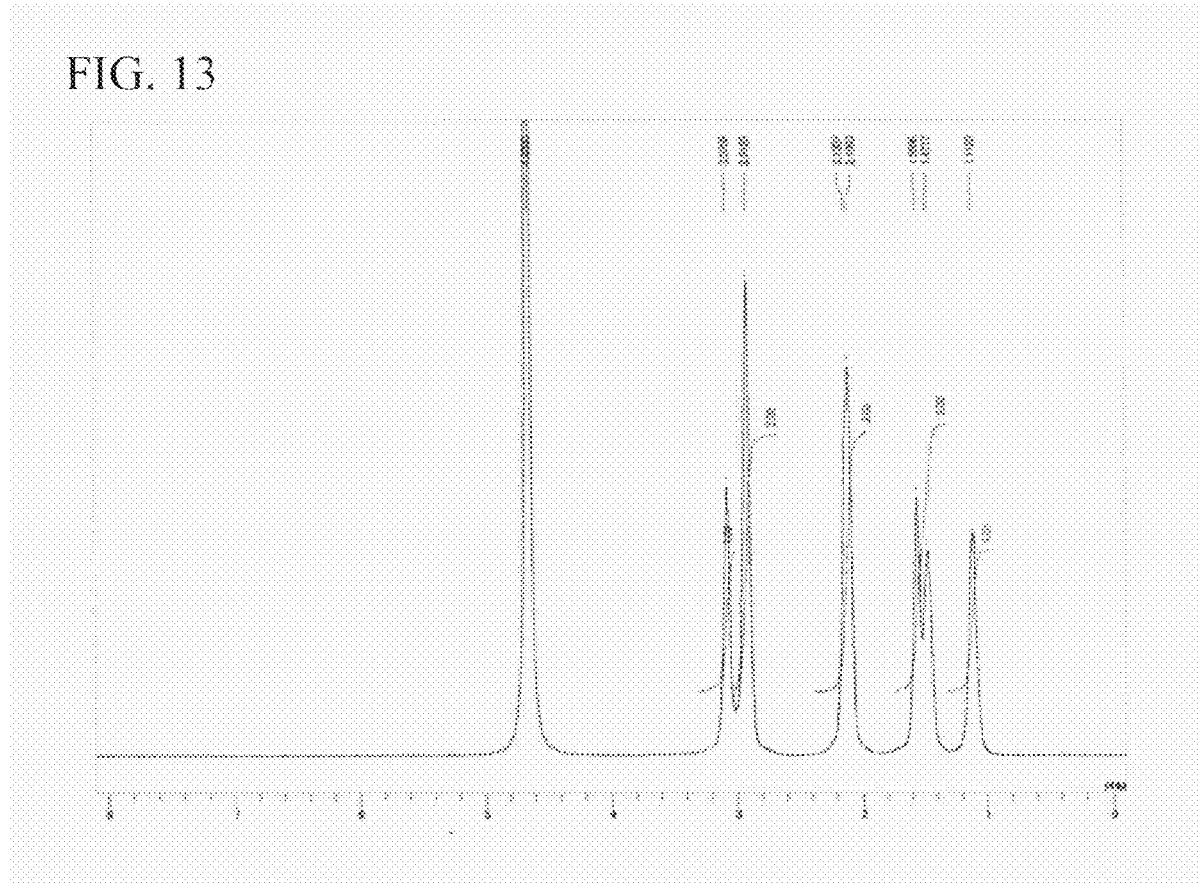
FIG. 13 is a $^1$H NMR spectrum of complex 3 in solution.
Figure 14:
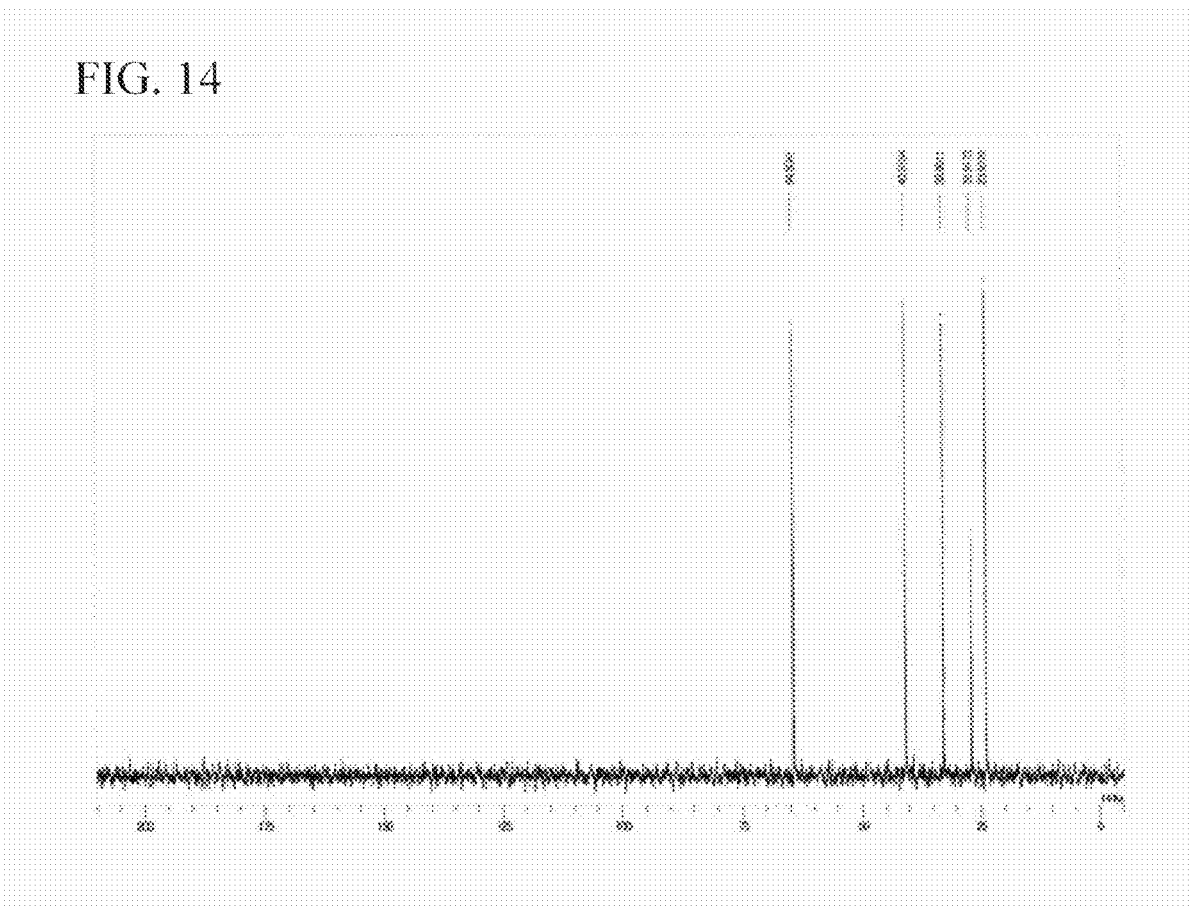
FIG. 14 is a $^{13}$C{$^1$H}NMR spectrum of complex 3 in solution.
Figure 15A:
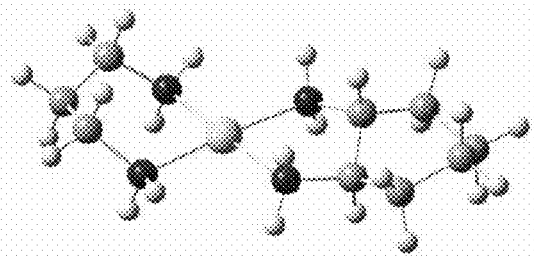
FIG. 15A shows a configuration of [(DACH)Au(pn)]$^{3+}$, where one of the ligands is trans-diaminocyclohexane.
Figure 15B:
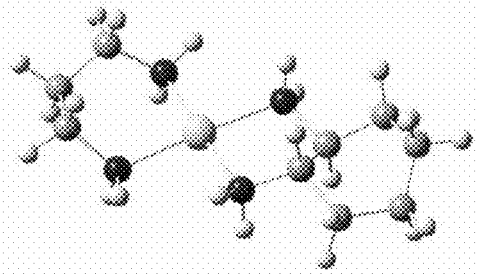
FIG. 15B shows a configuration of [(DACH)Au(pn)]$^{3+}$, where one of the ligands is trans-diaminocyclohexane.
Figure 15C:
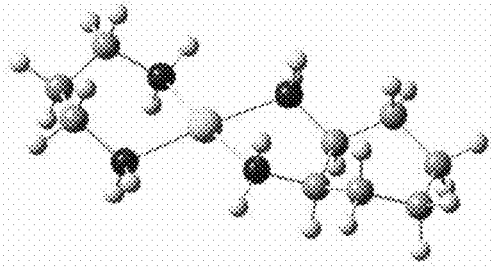
FIG. 15C shows a configuration of [(DACH)Au(pn)]$^{3+}$, where one of the ligands is cis-diaminocyclohexane.
Figure 15D:
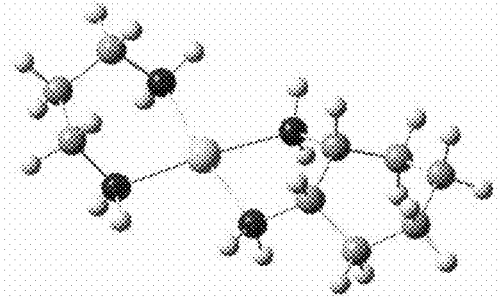
FIG. 15D shows a configuration of [(DACH)Au(pn)]$^{3+}$, where one of the ligands is cis-diaminocyclohexane.

All the $^1$H NMR spectra supported the structures of the synthesized complexes as indicated by the integration of the signals of C—H protons connected to the amino groups of the DACH and pn ligands. For instance, the ratio of the protons attached to amino group in both DACH and pn for complex 3 is 1:2 as depicted in FIG. 13. Its $^{13}$C NMR spectrum is also confirmed the structure as shown in FIG. 14. The $^1$H and $^{13}$C NMR chemical shifts of compounds 1-3 along with their corresponding free ligands are listed in Tables 5 and 6, respectively. In the $^1$H and $^{13}$C NMR spectra of complexes 1, 2 and 3, one half of the total expected signals were noticed because of the C$_2$ symmetry axis. 1,2-diaminocyclohexane ring is considered as a rigid conformer that allowed, for instance, to distinguish equatorial H3 and H6 from axial H3 and H6 at room temperature. The signals of C—H protons connected to the amino groups for DACH occur in the spectra at 3.07 to 3.65 ppm, shifting downfield compared with the corresponding signals (2.23-2.25 ppm) in the free DACH ligand. On the other hand, the signals of C—H protons connected to the amino groups for pn occur in the spectra at 2.91 to 2.94 ppm, shifting slightly upfield compared with the corresponding signals (2.98 ppm) in the free pn ligand.

The significant downfield shift was observed at 3.62 ppm for complex 1 with respect to the free DACH ligand at 2.23 ppm. This can be attributed to the donation of nitrogen lone pairs to the gold that causes de-shielding of the proton(s) next to the bonding nitrogen. On the other hand, $^{13}$C NMR downfield shift was observed only for the carbon next to the bonding nitrogen and the others carbons in the complex for DACH showed upfield shift. For instance, chemical shift of C3 and C4 for complex 1 observed at 26.92 and 20.73 ppm, respectively, whereas, for free diamine ligand it occurs at 35.26 and 26.36 ppm. It is also worth mentioning that complexes 1-3, even though they have the same skeleton of DACH and pn, their NMR chemical shifts specifically for DACH ligands are not same due to a different stereochemistry upon complexation.

Example 5

Solid-State NMR Measurements $^{13}$C solid-state NMR spectra were recorded on a Bruker 400 MHz spectrometer at an ambient temperature of 25° C. Samples were packed into 4 mm zirconium oxide rotors. Cross polarization and high power decoupling were employed. Pulse delay of 7.0 s and a contact time of 5.0 ms were used in the CPMAS experiments. The magic angle spinning rates were 4 and 8 kHz. Carbon chemical shifts were referenced to TMS by setting the high frequency isotropic peak of solid adamantine to 38.56 ppm. The solid NMR data are given in Table 7.

TABLE 7

Solid $^{13}$C NMR chemical shifts of free ligands and (DACH)-gold(III)-(pn) complexes.

| Compound | C1, C2 | C3, C6 | C4, C5 | C1', C3' | C2' | Refs. |
|---|---|---|---|---|---|---|
| [{cis-1,2-(DACH)}AuCl$_2$]Cl | 66.20, 65.35 | 30.98 | 27.02, 22.12 | — | | b |
| 1 | 64.03 | 29.31 | 21.74 | 44.57 | 28.01 | a |
| [{trans-(±)-1,2-(DACH)}AuCl$_2$]Cl | 69.60 | 37.37 | 27.99 | — | | b |
| 2 | 66.80 | 37.35 | 28.09 | 45.76 | 28.09 | a |

TABLE 7-continued

Solid $^{13}$C NMR chemical shifts of free ligands and (DACH)-gold(III)-(pn) complexes.

| Compound | $^{13}$C($\delta$ in ppm) | | | | | |
|---|---|---|---|---|---|---|
| | C1, C2 | C3, C6 | C4, C5 | C1', C3' | C2' | Refs. |
| {(1S2S)-(+)-1,2-(DACH)}AuCl$_2$]Cl | 70.21 | 37.86 | 29.16 | — | | b |
| 3 | 67.31, 64.41 | 36.05, 34.10 | 27.92 | 45.65 | 27.92 | a |

$^a$this work,
$^b$Al-Jaroudi SS et al. (2013) Polyhedron 50: 434-442 - incorporated herein by reference in its entirety.

At the spinning rate of 4 kHz, the isotropic signals for all complexes were not observed for the carbons, indicating the absence of the anisotropy that could take place due to the sp$^3$ hybridization of these atoms. Solid state NMR spectrum of complexes 1 and 2 showed equivalency in the chemical shifts of carbon atoms (C1,C2), (C3,C6), (C4,C6) and (C1', C2') two sets of peaks, whereas, similar observation did not attain for carbon atoms of DACH in complex 3 as listed in Table 7. This indicates that complex 3 in the solid state lacks C$_2$ symmetry. In contrast, all synthesized complexes 1, 2 and 3 showed C$_2$ symmetry in the solution state as indicated earlier by solution $^1$H and $^{13}$C NMR.

Compared to solution chemical shifts, significant de-shielding in solid state is observed with similarity in the chemical shift among all synthesized complexes (Table 7) which is a clear indication of stability of the prepared complexes in solid state.

Example 6

Crystallographic Data

Figure 3:
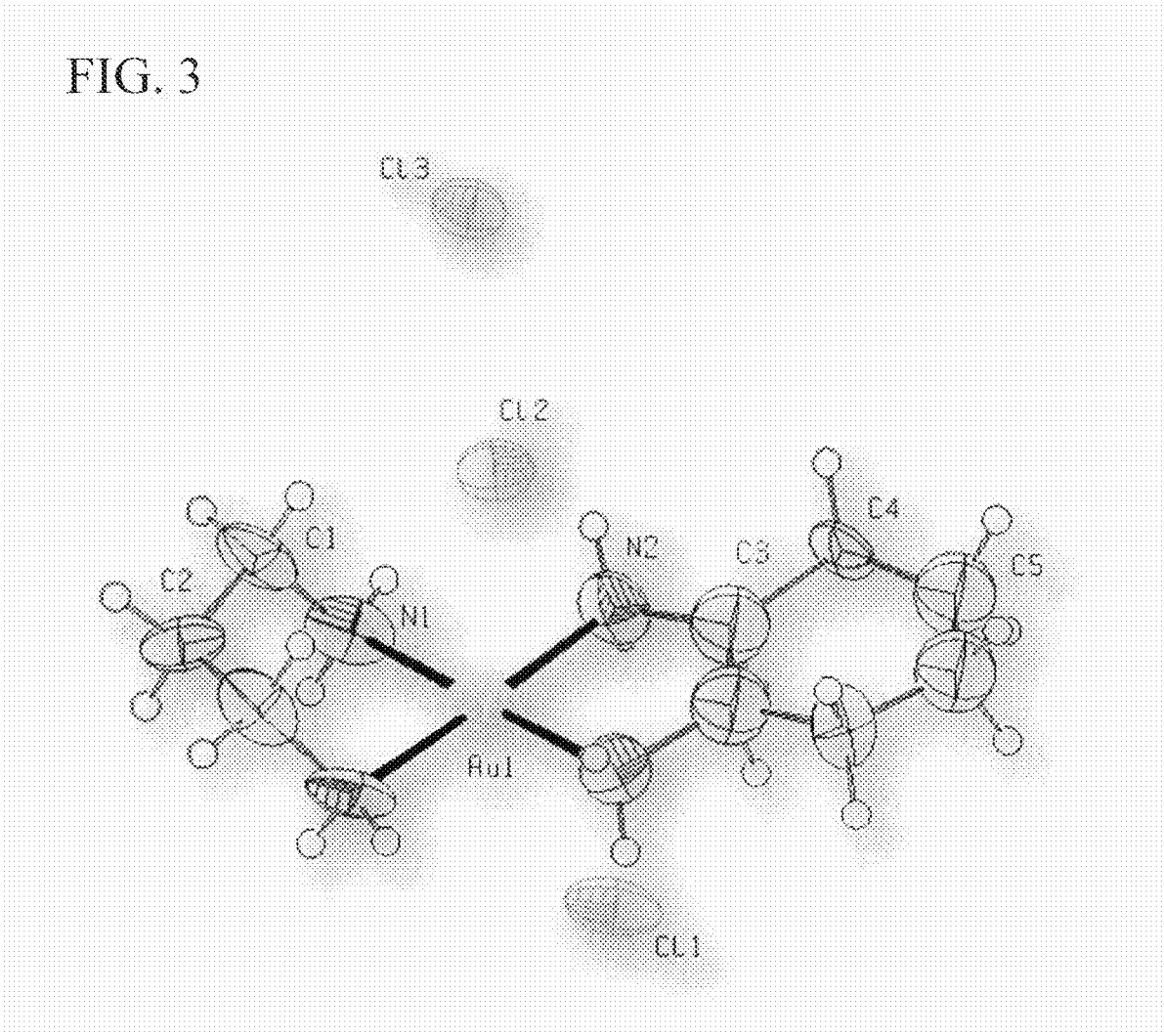
FIG. 3 is a view of the molecular structure of mononuclear complex 1, with partial atom labelling scheme and displacement ellipsoids drawn at 50% probability level.
Figure 4:
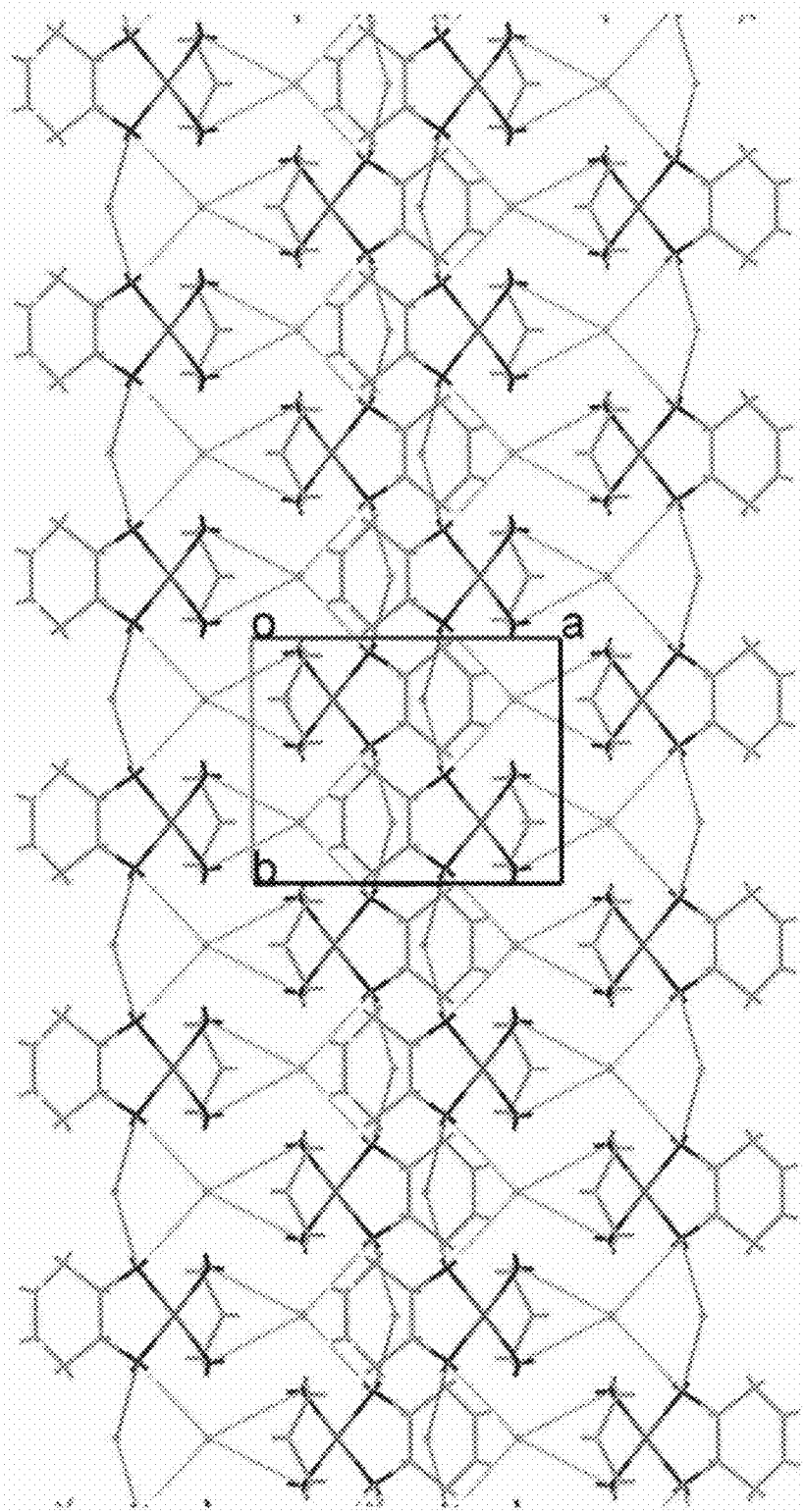
FIG. 4 is a view of the hydrogen bond network of complex 1 along the plane of the unit cell, with "o" denoting the cell origin, while "a" and "b" each denotes a cell vertex.

The intensity data were collected at 173 K on a two circle Stoe Image Plate diffraction system, using Mo—Kα graphite monochromated radiation. [Stoe, Cie, (2006) X-Area V1.35 and X-RED32 V1.31 Software, Stoe and Cie GmbH, Darmstadt, Germany—incorporated herein by reference in its entirety]. The structures were solved by direct methods, using the program SHELXS-97 [Sheldrick G M (2008) Acta Crystallogr. Sect. A 64:112-122—incorporated herein by reference in its entirety]. The refinement and all further calculations were carried out using SHELXL-97. The H-atoms were either located from Fourier difference maps and freely refined or included in calculated positions and treated as riding atoms using SHELXL default parameters. The non-H atoms were refined anisotropically, using weighted full-matrix least-squares on F$^2$. Empirical or multiscan absorption corrections were applied using and MULSCANABS routines in PLATON [Spek A L (2009) Acta Crystallogr. Sect. D 65:148-155—incorporated herein by reference in its entirety]. A summary of crystal data and refinement details for compound 1 are given in Table 8. FIGS. 3 and 4 were drawn using the programs PLATON and MERCURY [Macrae C F, Edgington P R, McCabe P, Pidcock E, Shields G P, Taylor R, Towler M, van de Streek J (2006) Appl. Cryst. 39:453-457—incorporated herein by reference in its entirety]. Selected bond-distances and bond angles are given in Table 9.

TABLE 8

Crystallographic data for compound 1

| | |
|---|---|
| Empirical formula | C$_9$H$_{24}$AuCl$_3$N$_4$ |
| Formula weight | 491.64 |
| Crystal size/mm | 0.15 × 0.3 × 0.09 |
| Wavelength/Å | 0.71073 |
| Temperature/K | 173 (2) |
| Crystal symmetry | Monoclinic |
| Space group | P21/m |
| a/Å | 10.139 (2) |
| b/Å | 7.2586 (11) |
| c/Å | 11.458 (4) |
| α/° | 90 |
| β/° | 115.55 (2) |
| γ/° | 90 |
| V/ Å$^3$ | 760.8 (3) |
| Z | 4 |
| D$_c$/Mg m$^{-3}$ | 2.146 |
| μ(Mo-Kα)/mm$^{-1}$ | 6.92 |
| F(000) | 472 |
| θ Limits/° | 2.0-25.7 |
| Collected reflections | 5312é |
| Unique reflections(R$_{int}$) | 985 (0.269) |
| Observed reflections [F$_o$ > 2σ(F$_o$)] | 1565 |
| Goodness of fit on F$^2$ | 1.05 |
| R$^1$(F), $^a$[I > 2σ (I)] | 0.158 |
| wR$_2$(F$^2$), $^b$[I > 2σ(I)] | 0.407 |
| Largest diff. peak, hole/e Å$^{-3}$ | 7.02-2.72 |

TABLE 9

Selected bond distances and bond angles for complex 1.

| Bond length (Å), found [Calc.] | | | | Bond angles (°), found [Calc.] | | | |
|---|---|---|---|---|---|---|---|
| Au1—N1 | 2.03 | (3) | [2.147] | N1—Au1—N1$^i$ | 87 | (2) | [88.9] |
| Au1—N1$^i$ | 2.03 | (3) | [2.147] | N1—Au1—N2$^i$ | 177.8 | (15) | [174.2] |
| Au1—N2$^i$ | 2.01 | (3) | [2.138] | N1$^i$—Au1—N2$^i$ | 93.2 | (15) | [96.9] |
| Au1—N2 | 2.01 | (3) | [2.137] | N1—Au1—N2 | 93.2 | (15) | [96.9] |
| N1—C1 | 1.54 | (6) | [1.537] | N1$^i$—Au1—N2 | 177.8 | (15) | [174.2] |
| N2—C3 | 1.48 | (6) | [1.545] | N2$^i$—Au1—N2 | 87 | (2) | [76.3] |
| | | | | C1—N1—Au1 | 113 | (2) | [115.9] |
| | | | | C3—N2—Au1 | 109 | (3) | [111.3] |

Example 7

Simulating the Structures of Gold(III) Complexes

The structures of the [(DACH)Au(pn)]$^{3+}$ complex with four possible conformations (cis-SR, cis-RS, trans-SS and trans-RR) were calculated without any geometrical constrains using GAUSSIAN09 program [Frisch M J et al. (2009) Gaussian 09, Revision A1 Gaussian Inc Wallingford CT; Giovagnini L, Ronconi L, Aldinucci D, Lorenzon D, Sitran S, Fregoni D J (2005) J. Med. Chem. 48:1588-1592. Gulloti M, Pasini A, Ugo R, Filippeschi S, Marmonti L, Spreafico F (1984) Inorg. Chim. Acta 91: 223-227, incorporated herein by reference in its entirety]. The hybrid B3LYP density functional (the three-parameter Becke functional with correlation from the Lee-Yang-Parr functional) with the Los Alamos National Laboratory-2 double-ζ (LANL2DZ) basis set was employed in this study [Wadt W R, Hay P J (1985a) J. Chem. Phys. 82:270-283; Wadt W R, Hay P J (1985b) J. Chem. Phys. 82:284-298; and Wadt W R, Hay P J (1985c) J. Chem. Phys. 82:299-305; Lee C, Yang W Parr R G (1988) Phys. Rev. B 37(2):785—each incorporated herein by reference in its entirety]. We reported results for some gold-based complexes at this level of calculations giving decent results that are consistent with our experimental finding (Al-Jaroudi S S, Monim-ul-Mehboob M, Altaf M, Al-Saadi A A, Wazeer M I M, Altuwaijri S, Isab A A (2014) Biometals 27:1115-1136—incorporated herein by reference in its entirety). Moreover, stationary points have been confirmed by frequency calculation. Calculated bond distances and angles are listed alongside with experimental values in Table 9 for compound 1, while Table 10 compares the relative stabilities based on the calculated energies of the optimized minimum structures.

TABLE 10

Relative energies (kcal/mol) of the four possible conformations of the [(DACH)Au(pn)]$^{3+}$ complex.

| Conformation | Relative Energy (kcal/mol) |
|---|---|
| a, b | 0.00 |
| c | 3.31 |
| d | 3.59 |

The optimized structures of the [(DACH)Au(pn)]$^{3+}$ complexes as obtained from the B3LYP/LANL2DZ level of calculations are shown in FIGS. 15A to 15D. The molecular crystal structure of complex [(DACH)Au(pn)].3Cl 1 is shown in FIG. 3. It is a mononuclear complex containing one trans 1,2-cyclohexanediamine(DACH) and 1,3-propanediamine(pn) ligand molecules. There are three chloride ions in the outer sphere of the complex. The coordination geometry around the gold(III) ion is pseudo-square planar as confirmed by crystallographic data and supported by density functional calculations and central gold(III) atom is coordinated with four NH$_2$ donor groups of the trans 1,2-cyclohexanediamine and 1,3-propanediamine mixed ligand molecules. There is a good agreement between the experimental and calculated structural parameters for almost all bond distances and angles, which provides more support to the crystallographic findings (Table 9). The mononuclear cation contains one five-membered chelate cycle AuN2C2 and one six-membered chelate cycle AuN2C3.

Au1-N1 and Au1-N2 bond distances are 2.03 (3) & 2.01(3) Å, respectively, in a good agreement with the calculated DFT values (2.145 & 2.144). The N1-Au1-N1i & N2-Au2-N2i bond angles are 87 (2)°. The bond angles around gold (III) ion in mononuclear complex 1 are unexpectedly same. These observations provide an additional evidence for the presence of centro-symmetric geometry in complex 1.

From the computed energetics of the four structures of the complex 1-3 (Table 10), the trans conformations are more preferable compared to the cis conformations with more than 3.59 kcal/mol difference. The most possible explanation of this energy variation is the ring configuration of the DACH ligand, where in the cis form the CH$_2$ units experience more steric repulsion compared to the trans form.

Example 8

Stability Studies of the Gold(III) Complexes

Compounds 1, 2 and 3 were tested for their stability in water as well as mixed solvents of DMSO/water (2/1 v/v ratio) solution by $^{13}$C and $^1$H NMR. The compounds are highly soluble in water but sparingly soluble in DMSO. The hydroscopic nature of DMSO could unfortunately lead to stability issue [Ellson R, Stearns R, Mutz M, Brown C, Browning B, Harris D, Qureshi S, Shieh J, Wold D (2005) Comb. Chem. High Throughput Screen, 8:489-498—incorporated herein by reference in its entirety]. To investigate the structural stability of the compounds, NMR spectra of the compounds dissolved in D$_2$O and mixed DMSO-d$_6$/D$_2$O (v/v: 2/1) solvents were obtained on immediate dissolution and latter at 24 h and after three days 72 h at room temperature in mixed DMSO-d$_6$/D$_2$O and at 37° C. in D$_2$O. A minimum of 30 mg/mL of representative gold(III) compounds 1, 2 and 3 were subjected to $^1$H and $^{13}$C NMR spectra analysis followed by dissolution in D$_2$O and DMSO-d$_6$/D$_2$O (v/v: 2/1, 1 mL). The duplicate samples were dissolved and immediately stored at room temperature and 37° C., respectively, and followed by determination of stability through NMR measurements for compounds 1, 2 and 3 over time periods of 24 h and 72 h.

Figure 16A:
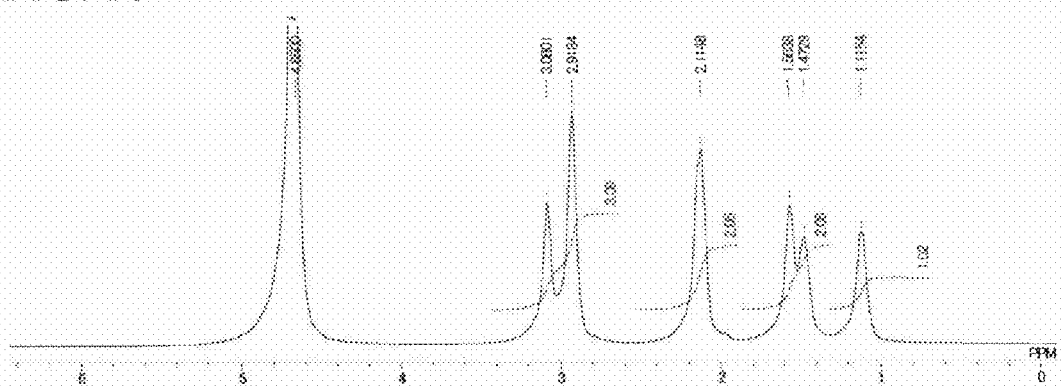
FIG. 16A is a $^1$H NMR spectrum of complex 3 in D$_2$O, taken immediately after dissolution.
Figure 16B:
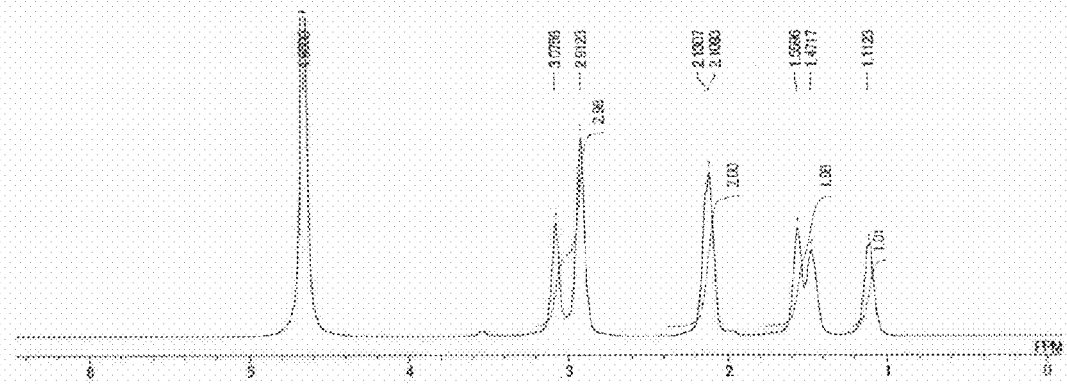
FIG. 16B is a $^1$H NMR spectrum of complex 3 in D$_2$O, taken 7 days after dissolution.
Figure 17A:
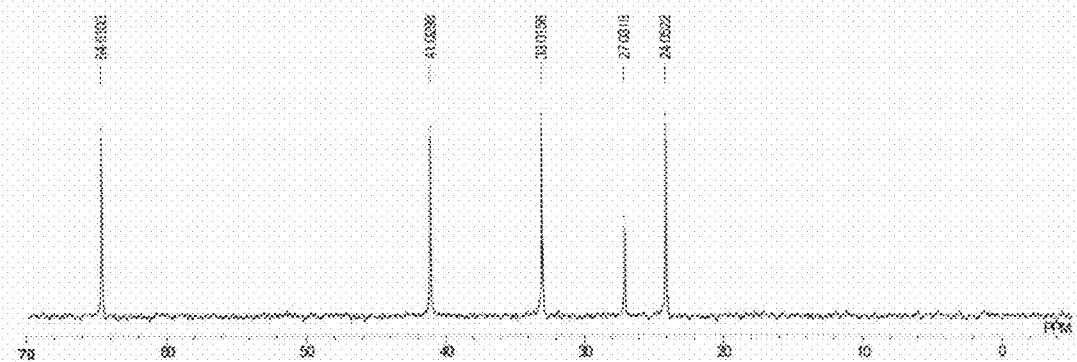
FIG. 17A is a $^{13}$C{$^1$H} NMR spectrum of complex 3 in D$_2$O, taken immediately after dissolution.
Figure 17B:
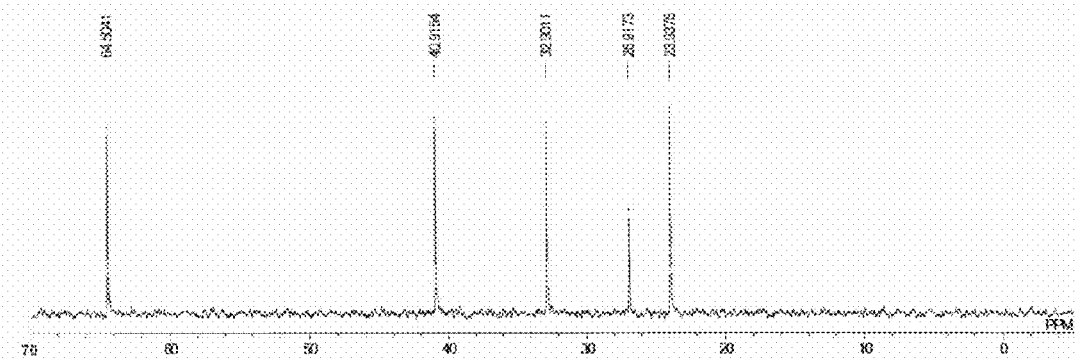
FIG. 17B is a $^{13}$C{$^1$H} NMR spectrum of complex 3 in D$_2$O, taken 7 days after dissolution.
Figure 18A:
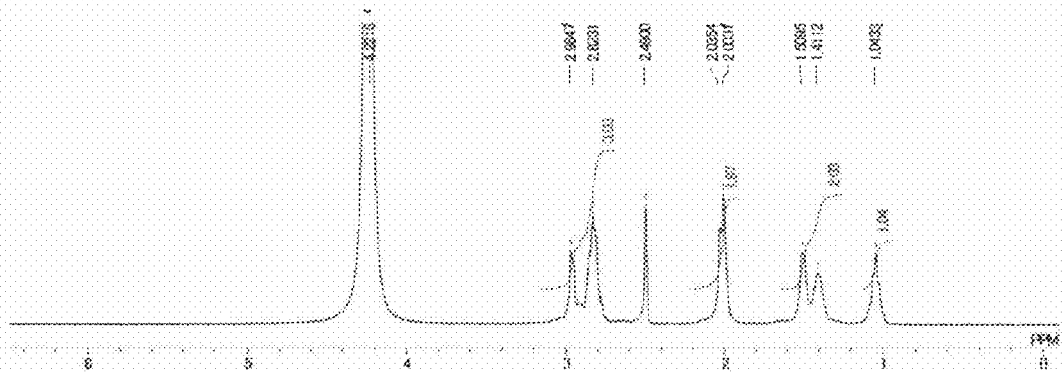
FIG. 18A is a $^1$H NMR spectrum of complex 3 in DMSO-d$_6$/D$_2$O, taken immediately after dissolution.
Figure 18B:
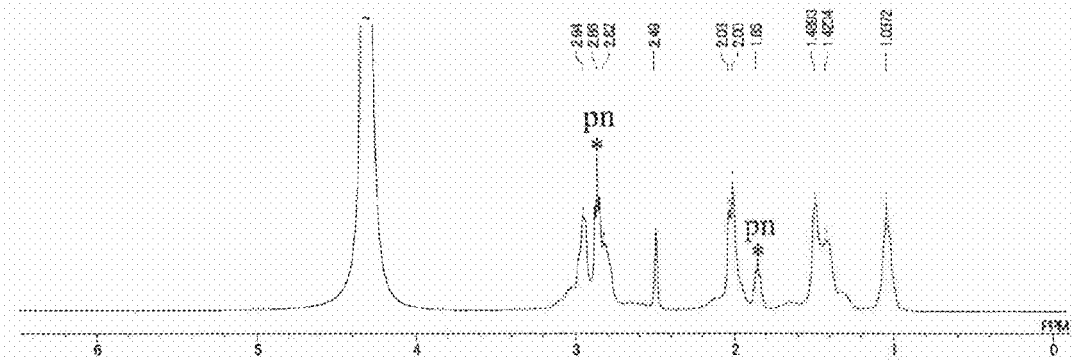
FIG. 18B is a $^1$H NMR spectrum of complex 3 in DMSO-d$_6$/D$_2$O, taken 7 days after dissolution.
Figure 19A:
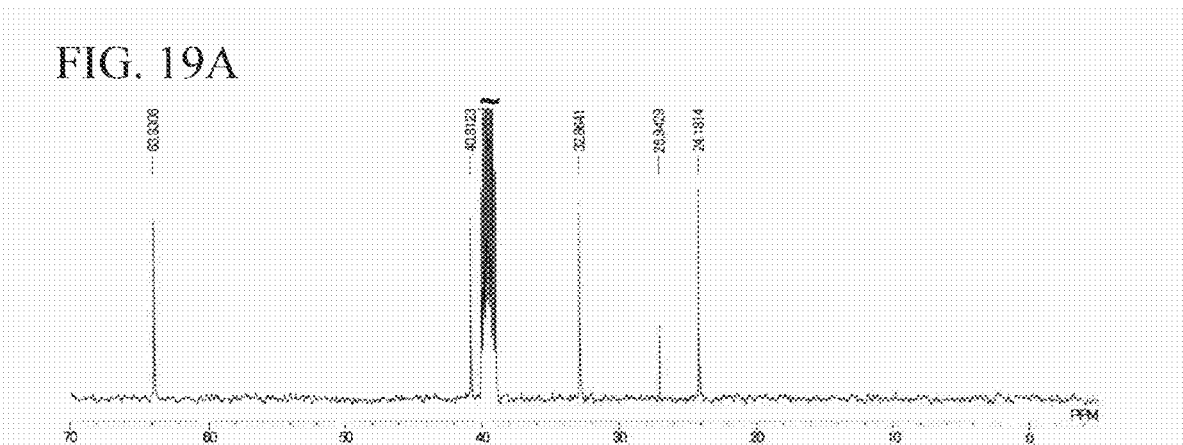
FIG. 19A is a $^{13}$C{$^1$H} NMR spectrum of complex 3 in DMSO-d$_6$/D$_2$O, taken immediately after dissolution.
Figure 19B:
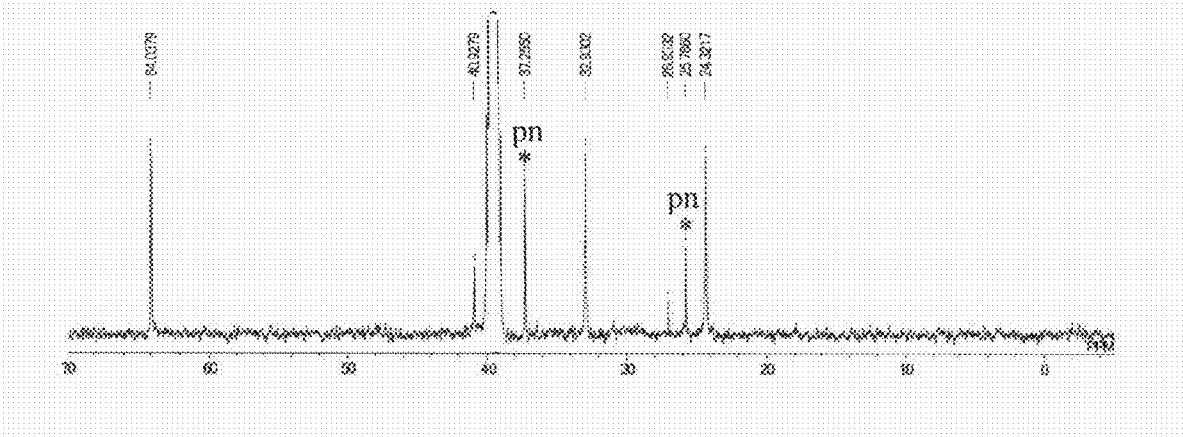
FIG. 19B is a $^{13}$C{$^1$H} NMR spectrum of complex 3 in DMSO-d$_6$/D$_2$O, taken 7 days after dissolution.

The NMR spectra of the complexes were obtained upon immediate dissolution to serve as reference spectra and later at 24 h and after 7 days at 37° C. in D$_2$O and at room temperature in mixed DMSO-d$_6$/D$_2$O in order to determine their stability. In general, all complexes showed high stability in D$_2$O as well as in mixed DMSO-d$_6$/D$_2$O and their NMR profiles remained unchanged over the span of 7 days. For example, FIGS. 16 and 17 illustrate the $^1$H and $^{13}$C NMR profiles of the compound 3, just after mixing and after 7 days respectively. Whereas, these compounds in mixed DMSO-d$_6$/D$_2$O solvent system were less stable at the experimental conditions, in which, dissociation of 1,3-propylenediamine from the gold complexes was observed in 24 h. On the other hand, no dissociation was observed for diaminocyclohexane. Among all synthesized complexes, the maximum dissociation for 1,3-propylenediamine after 7 days was experienced for compound 3 with approximately 50%. $^1$H and $^{13}$C NMR profiles of compound 3 in DMSO-d$_6$/D$_2$O at just after mixing and after 7 days are shown in FIGS. 18 and 19 respectively. $^1$H and $^{13}$C NMR spectra of compound 3 spectra after 7 days in DMSO-d$_6$/D$_2$O showed an extra peak at 2.86, 1.86 ppm and 37.26, 25.77 ppm as shown in FIGS. 16B and 17B, respectively, corresponding to the free 1,3-propylenediamine atoms. It is clearly concluded that the bond between gold(III) and diaminocyclohexane is stronger than the bond between gold(III) and 1,3-propylenediamine in these complexes 1-3, suggesting that 1,3-propylenediamine could be a better leaving group in these mixed ligands complexes.

Example 9

Electrochemistry of Gold(III) Complexes

The electrochemical experiments were performed at room temperature using a potentiostat (SP-300, BioLogic Science Instruments) controlled by EC-Lab v10.34 software package. The electrochemical experiments were performed at room temperature. All the measurements were performed on solutions deaerated by bubbling ultra-pure nitrogen for 15 min. The values of potential here reported were measured against a saturated calomel electrode (SCE). The cyclic voltammetry of the compounds 1, 2 and 3 were measured at scan rate of 50 mV/s on a reference buffer (40 mM phosphate, 4 mM NaCl, pH 7.4) using platinum as working electrode and graphite as a counter electrode with a concentration of 1.0 mM at room temperature. Ferrocene was used as pseudo reference to calibrate the working electrode. The couple $Fe^{III/II}$ formal potential of ferrocene occur at $E^{o'}=+0.44$ V (vs SCE) in 0.1M $Bu_4NPF_6$ solution in acetonitrile which is similar to the report value under the same experimental condition [Hans J, Beckmann A, Krüger H J (1999) Eur. J. Inorg. Chem. 163-172—incorporated herein by reference in its entirety]. Conversion to values vs NHE was obtained upon adding +0.24 V to the corresponding SCE values.

Figure 20A:
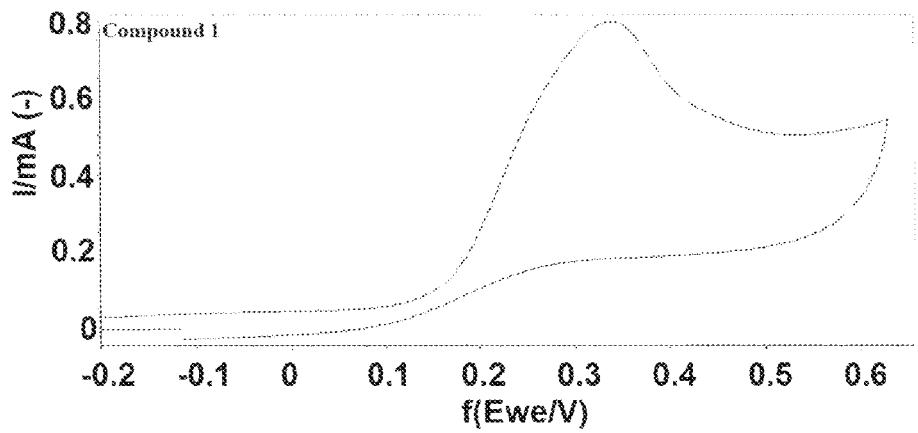
FIG. 20A is a cyclic voltammogram of complex 1 dissolved in a phosphate buffer, with a working platinum electrode.
Figure 20B:
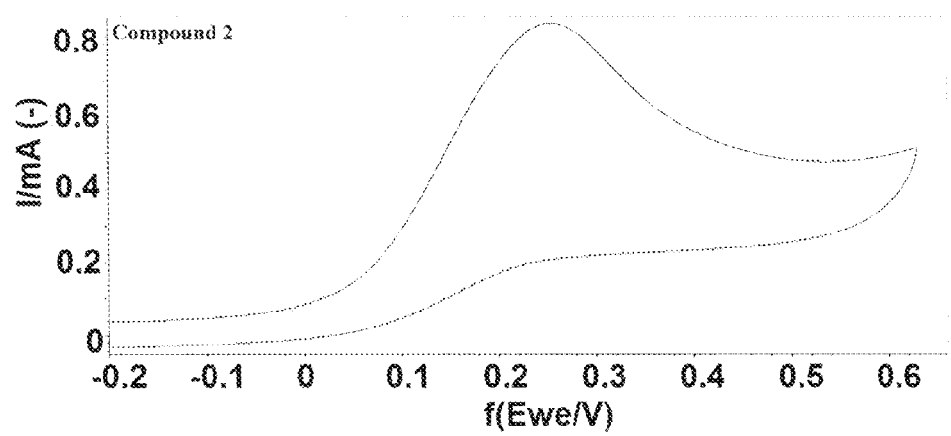
FIG. 20B is a cyclic voltammogram of complex 2 in dissolved in a phosphate buffer, with a working platinum electrode.
Figure 20C:
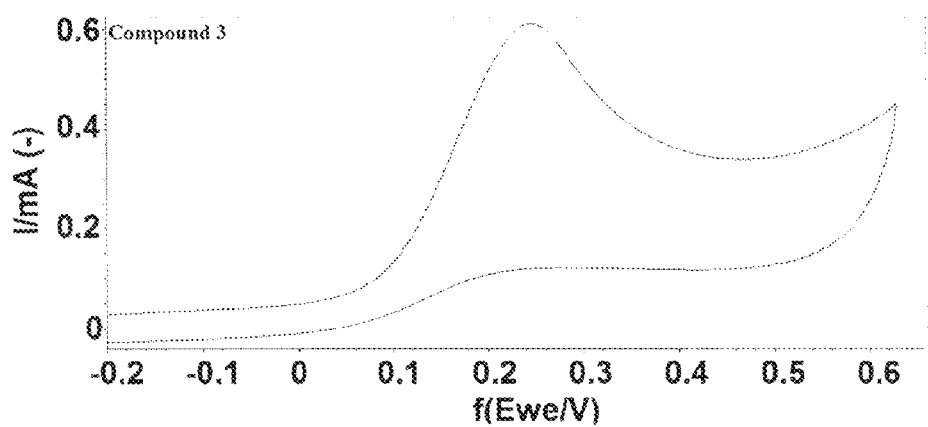
FIG. 20C is a cyclic voltammogram of complex 3 in dissolved in a phosphate buffer, with a working platinum electrode.

The electrochemical behavior of compounds 1, 2 and 3 was investigated in a physiological environment through cyclic voltammetry (CV). The cyclic voltammetric curves of the complexes 1, 2 and 3 are shown in FIGS. 20A to 20C. Table 11 summarizes the cyclic voltammetric data of all the studied compounds. The reduction potential values vs. NHE for the reduction processes exhibited by the complexes 1, 2 and 3, in a reference phosphate buffer solution, were in the range (+0.24)-(+0.34) V. Cyclic voltammetric data indicated that cis-1,2-DACH conformer is slightly more stable than the trans-1,2-DACH conformer of the complexes. Gold(III) complexes 1, 2 and 3 show one irreversible reduction process in which the controlled potential coulometry involves three electrons per mole. The occurrence of Au(III)/Au(0) reduction is visually indicated by the appearance of a thin gold layer deposited on the platinum electrode surface after exhaustive electrolysis (Ew, −0.7 V). In general, cyclic voltammetric results suggest that these compounds are fairly stable under the physiological conditions.

TABLE 11

Peak potential values vs. NHE for reduction of gold(III) complexes

| Complex | $E_p(V)$ |
|---|---|
| 1 | 0.34 |
| 2 | 0.25 |
| 3 | 0.24 |

The stability of the gold(III) compounds in the reference phosphate buffer was also checked after the addition of stoichiometric amounts of the biologically important reducing agent sodium ascorbate. It was observed that all complexes were quickly and almost completely reduced in 30 min.

Example 10

Cell Viability Studies

Human gastric SGC7901 cancer and prostate PC3 cancer cell lines were provided by American Type Culture Collection (ATCC). Cells were cultured in Dulbecco's Modified Eagle Medium (DMEM) supplemented with 10% fetal calf serum (FCS), penicillin (100 kU $L^{-1}$) and streptomycin (0.1 g $L^{-1}$) at 37° C. in a 5% $CO_2$-95% air atmosphere. MTT (3-(4,5-Dimethylthiazol-2-yl)-2,5-diphenyltetrazolium bromide, a yellow tetrazole) was purchased from Sigma Chemical Co, St. Louis, Mo., USA.

An MTT assay was used to obtain the number of living cells in the sample. Human gastric cancer SGC7901 and prostate cancer PC3 cells were seeded on 96-well plates at a predetermined optimal cell density, i.e. ca 6000 cells/1004 per well in 96-well plates, to ensure exponential growth in the duration of the assay. After 24 h pre-incubation, the growth medium was replaced with the experimental medium containing the appropriate drug, using one of 1,2-diaminocyclohexane(1,3-propylenediamine)gold (III) chloride compounds 1, 2 and 3 or a control using water. Six duplicate wells were set up for each sample, and cells untreated with drug served as a control. In one set of culture plates, human gastric cancer SGC7901 and human prostate PC3 cells were treated with 10 μM compounds 1, 2 and 3 as the drug and the control (water) for 24, 48 and 72 h. In other sets, the compounds 1, 2 and 3 with different concentration, i.e. 10, 20 and 30 μM, were employed to determine the growth inhibitory effect for both PC3 and SGC7901cells separately. After incubation, 10 μL MTT (6 g/L, Sigma) was added to each well and the incubation was continued for 4 h at 37° C. After removal of the medium, MTT stabilization solution [dimethylsulfoxide (DMSO):ethanol=1:1] was added to each well, and shaken for 10 min until all crystals were dissolved. Then, the optical density was detected in a micro plate reader at 550 nm wavelength using an Enzyme-Linked Immuno-Sorbent Assay (ELISA) reader. After being treated with the 1,2-diaminocyclohexane(1,3-propylenediamine) gold (III) chloride compounds 1, 2 and 3, the cell viability was examined by MTT assay. Each assay was performed in triplicate. An MTT assay for the inhibitory effect has been used for compounds 1, 2 and 3 against PC3 and SGC7901 cells. These cells were treated with various concentrations of compounds 1, 2 and 3 for 24-72 h. The p-value was less than 0.05, and the mean and standard deviation are calculated and represented in FIGS. 5 to 11.

Presently, gold-based chemotherapeutics studies are among the most widely prescribed drugs in modern oncology which aim towards designing newer compounds showing enhanced anti-proliferative potential and not as much of associated toxicity than cisplatin. In this aspect, gold (III) complexes with various ligands including Au—N, Au—S or Au—C bonds are being extensively developed and investigated for their bioactivities as antiproliferative agents [Burchenal J H, Kalaher K, O'Toole T Chisholm J (1977) Cancer Res. 37:3455-3457—incorporated herein by reference in its entirety]. In this work, a new series of gold(III) complexes (1-3) containing mixed 1,3-propylenediamine (pn) and 1,2-DACH ligands are being evaluated for antiproliferation against PC3 and SGC7901 cancer cell lines.

Figure 5A:
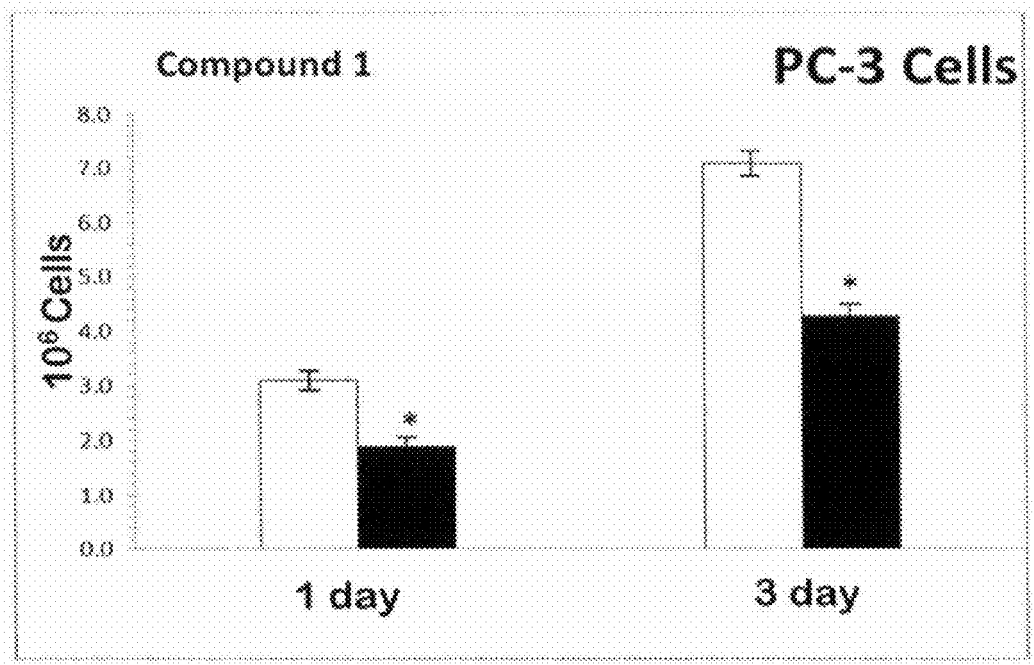
FIG. 5A is a bar graph showing the untreated PC3 cells (white bar) and the time-dependent antiproliferative effect of 10 μM complex 1 on PC3 cells (black bar) for 24 and 72 h.
Figure 5B:
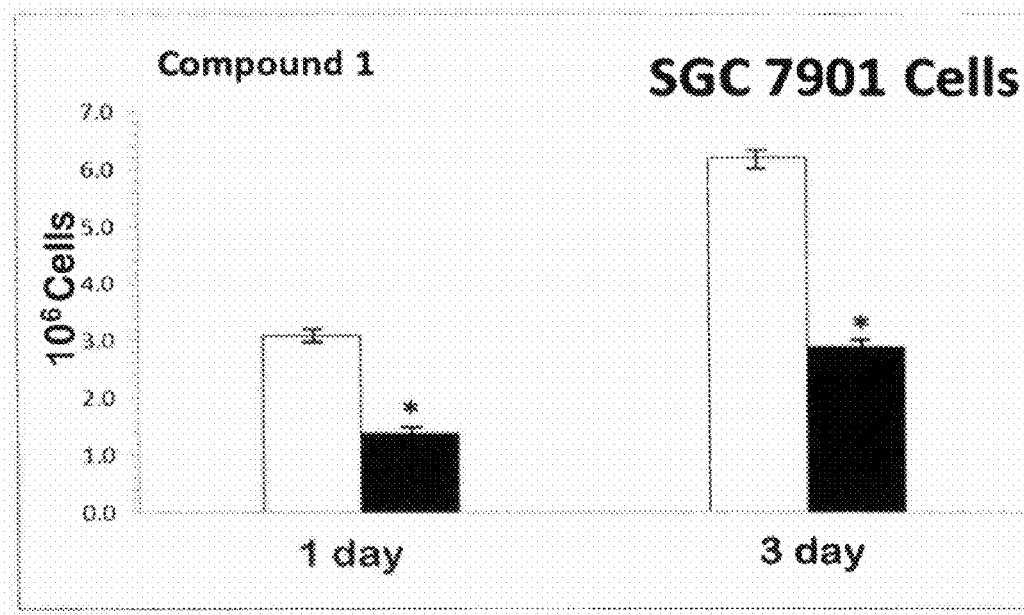
FIG. 5B is a bar graph showing the untreated SGC7901 cells (white bar) and the time-dependent antiproliferative effect of 10 μM complex 1 on SGC7901 cells (black bar) for 24 and 72 h.
Figure 6A:
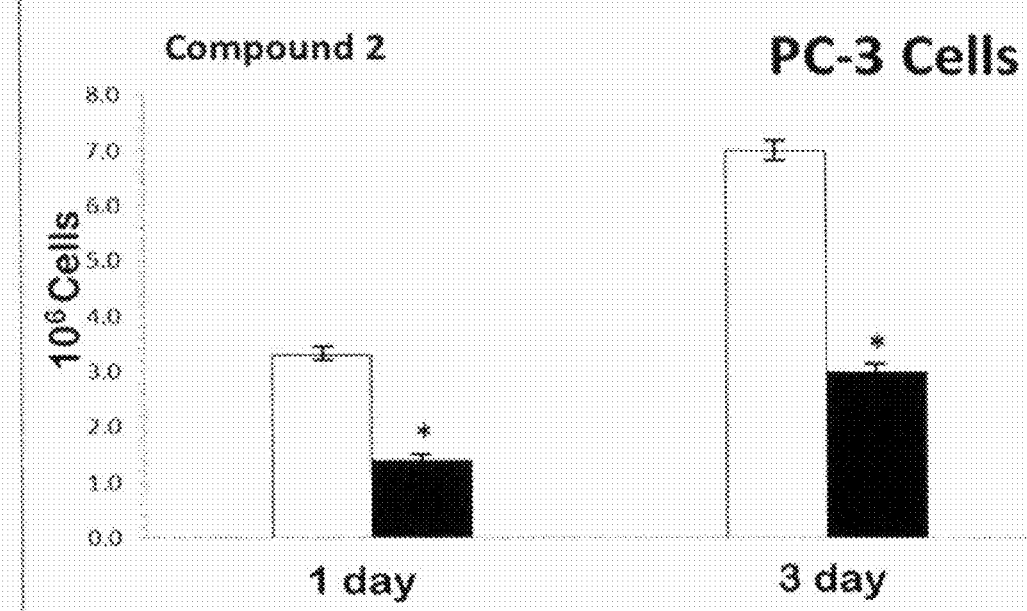
FIG. 6A is a bar graph showing the untreated PC3 cells (white bar) and the time-dependent antiproliferative effect of 10 μM complex 2 on PC3 cells (black bar) for 24 and 72 h.
Figure 6B:
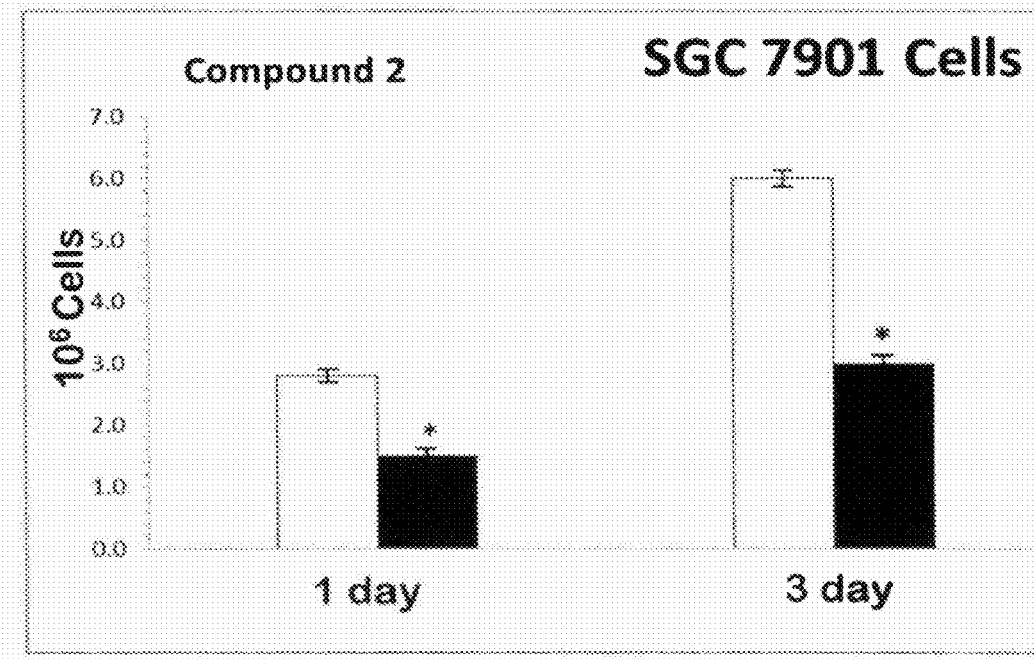
FIG. 6B is a bar graph showing the untreated SGC7901 cells (white bar) and the time-dependent antiproliferative effect of 10 μM complex 2 on SGC7901 cells (black bar) for 24 and 72 h.
Figure 7A:
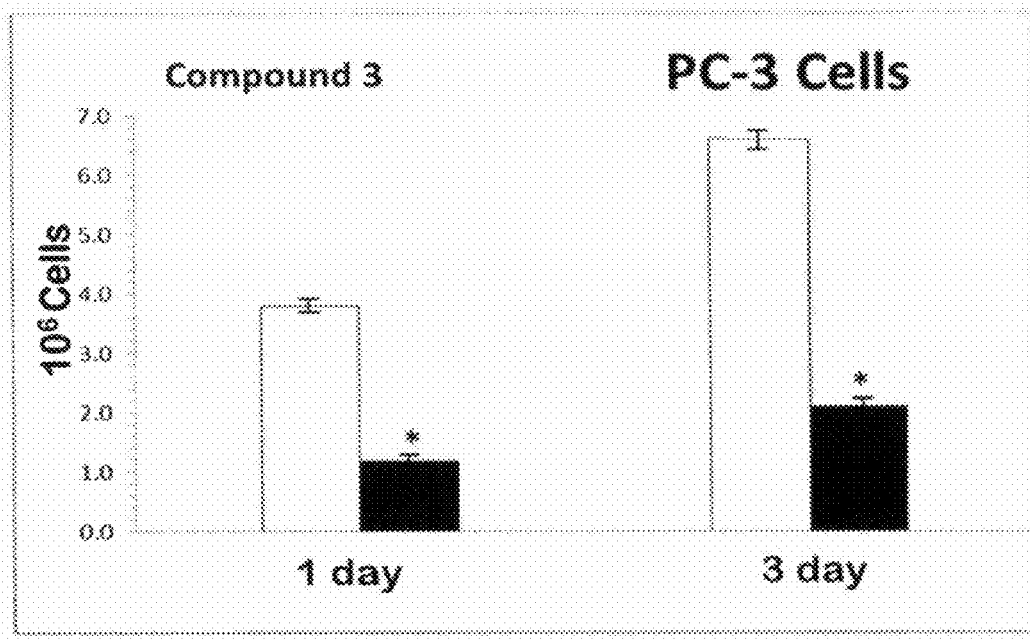
FIG. 7A is a bar graph showing the untreated PC3 cells (white bar) and the time-dependent antiproliferative effect of 10 μM complex 3 on PC3 cells (black bar) for 24 and 72 h.
Figure 7B:
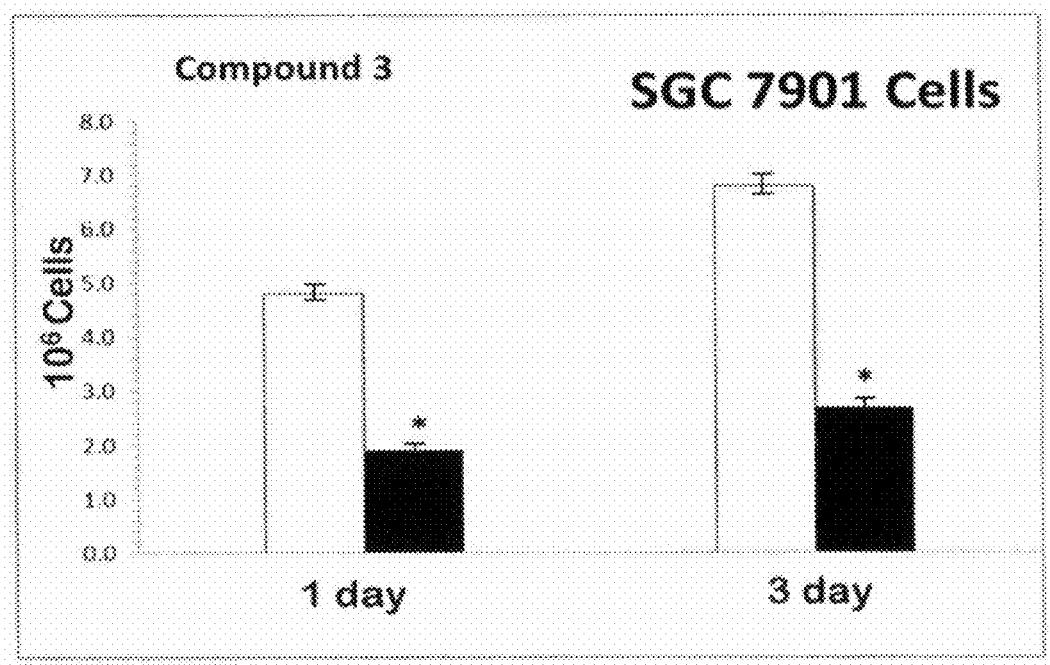
FIG. 7B is a bar graph showing the untreated SGC7901 cells (white bar) and the time-dependent antiproliferative effect of 10 μM complex 3 on SGC7901 cells (black bar) for 24 and 72 h.

FIGS. 5, 6 and 7 illustrate time dependent antiproliferative effects of complexes 1, 2 and 3 respectively. In the time dependent, the growth inhibition on PC3 and SGC7901cancer cells was studied using fixed concentration i.e. 10 μM. It is clearly evident from FIGS. 5, 6 and 7 that time dependent antiproliferative effects of trans-DACH complexes 2 and 3 on PC3 cancer cells are much better than those on SGC7901 cancer cells. However, it is vice versa for time dependent antiproliferative effects for cis-DACH complex 1. Complex 3 showed better cell inhibition against both PC3 and SGC7901 cell lines than complexes 1 and 2 as shown in FIGS. 5 to 7. Gold(III) complexes 2 and 3 demonstrated a comparable cell inhibition; against tested cell lines as shown in FIGS. 6 and 7, whether the complexes exposure time was 24 h or 72 h. All the gold(III) complexes showed lower cell inhibition against both cancer cell lines for 72 h exposure time compared to 24 h as shown in FIGS. 5 to 7.

Figure 8A:
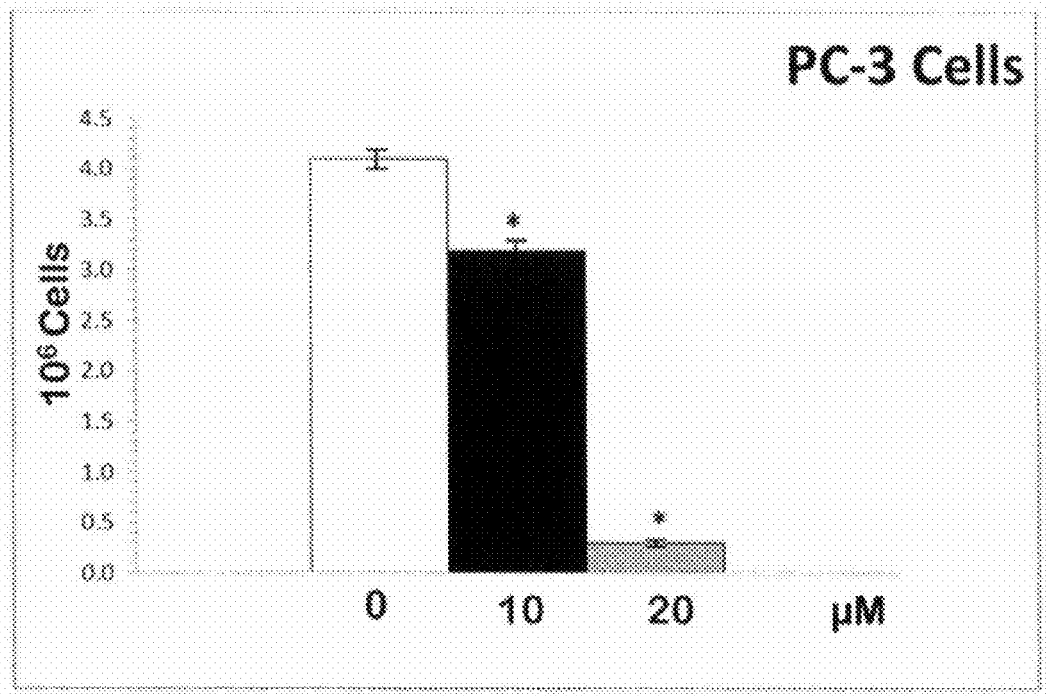
FIG. 8A is a bar graph showing the concentration-dependent antiproliferative effect of complex 1 on PC3 cells for 24 h.
Figure 8B:
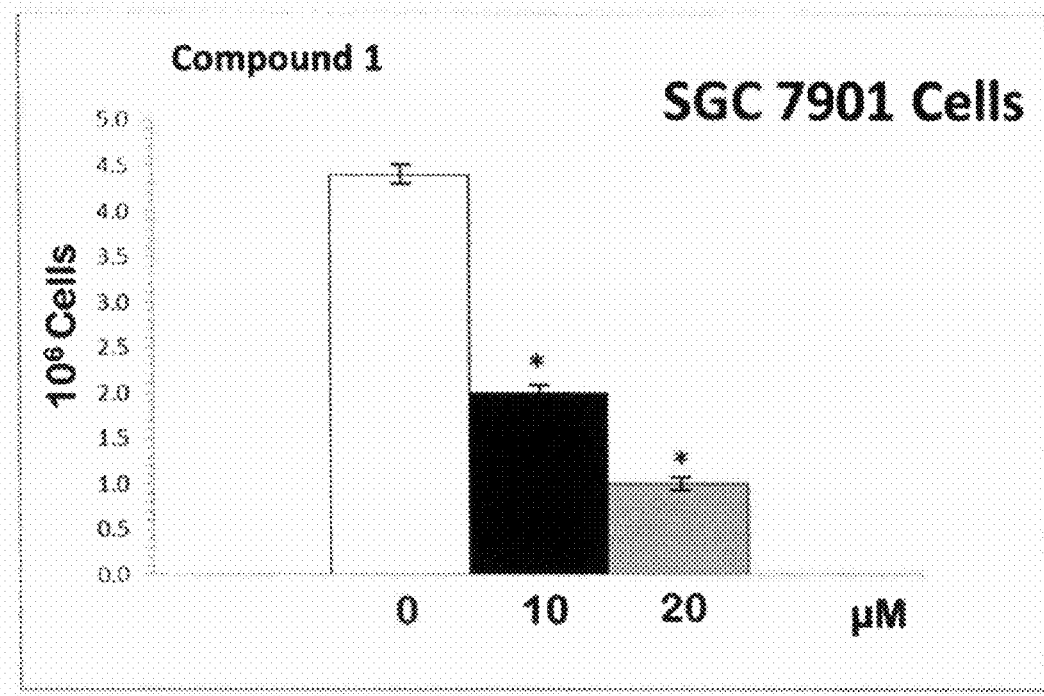
FIG. 8B is a bar graph showing the concentration-dependent antiproliferative effect of complex 1 on SGC7901 cells for 24 h.
Figure 9A:
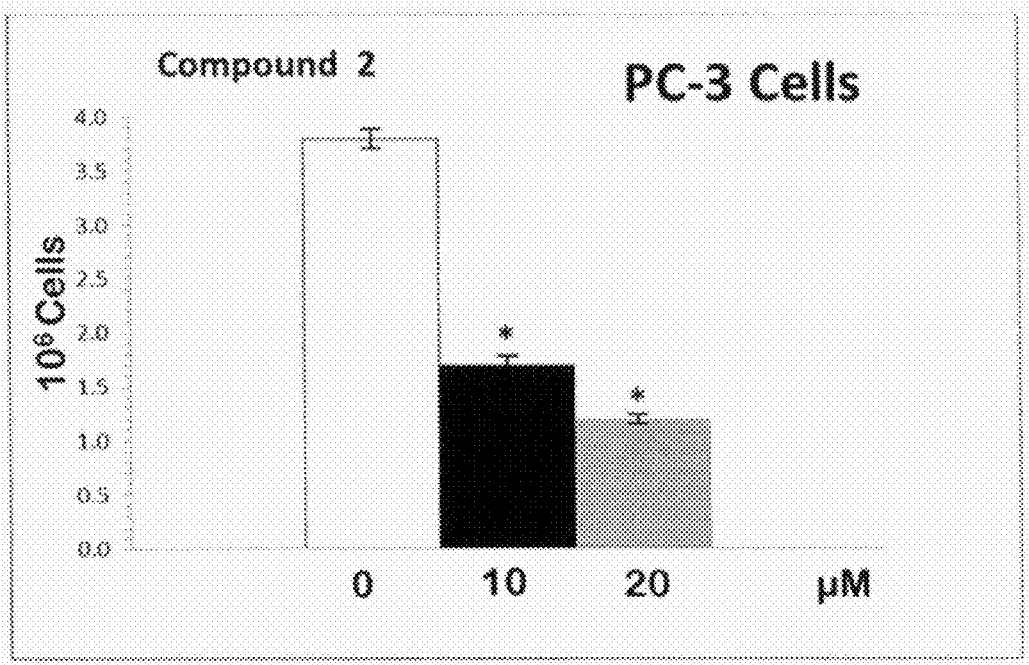
FIG. 9A is a bar graph showing the concentration-dependent antiproliferative effect of complex 2 on PC3 cells for 24 h.
Figure 9B:
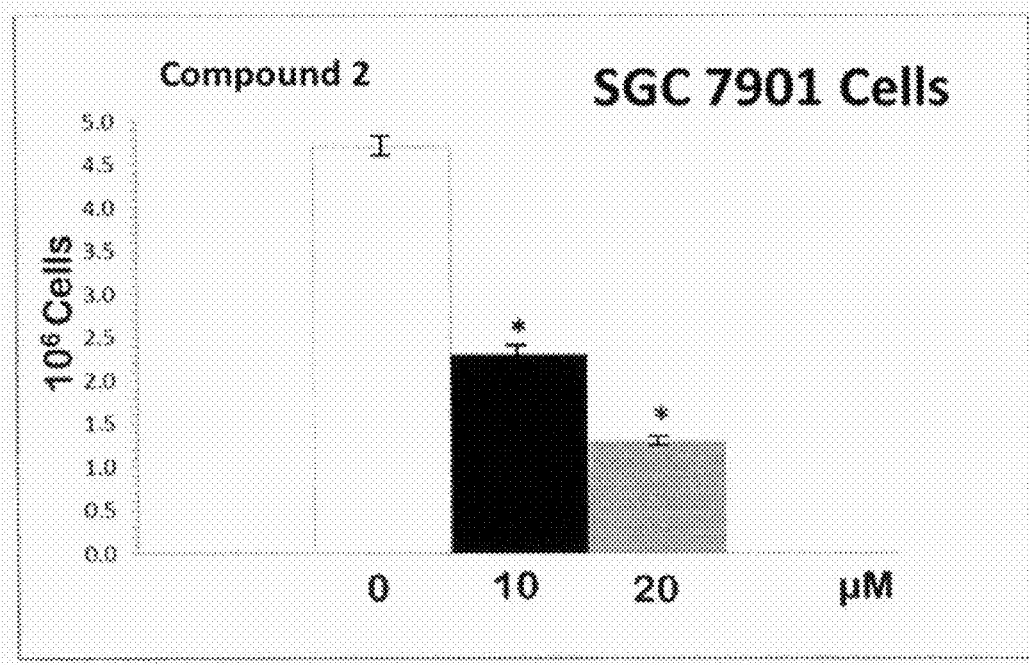
FIG. 9B is a bar graph showing the concentration-dependent antiproliferative effect of complex 2 on SGC7901 cells for 24 h.
Figure 10A:
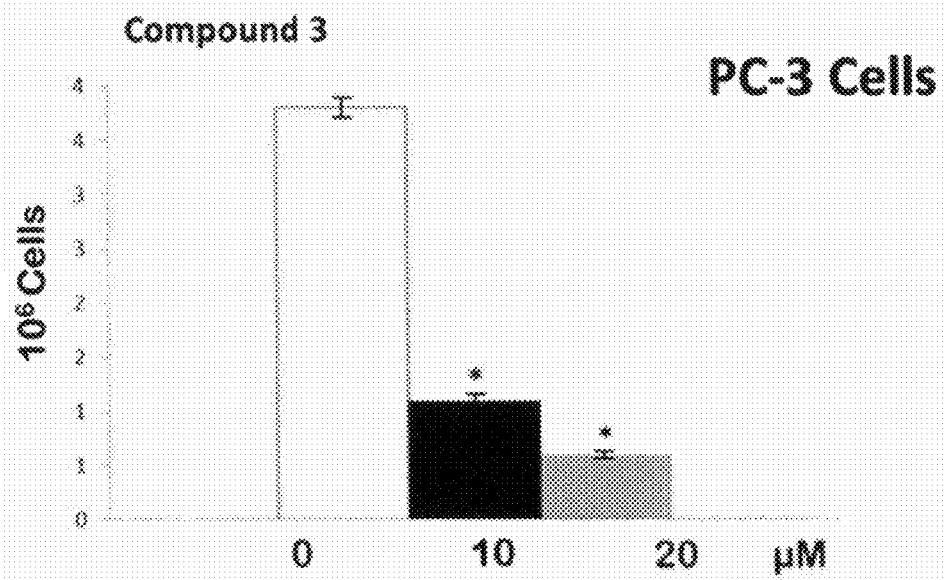
FIG. 10A is a bar graph showing the concentration-dependent antiproliferative effect of complex 3 on PC3 cells for 24 h.
Figure 10B:
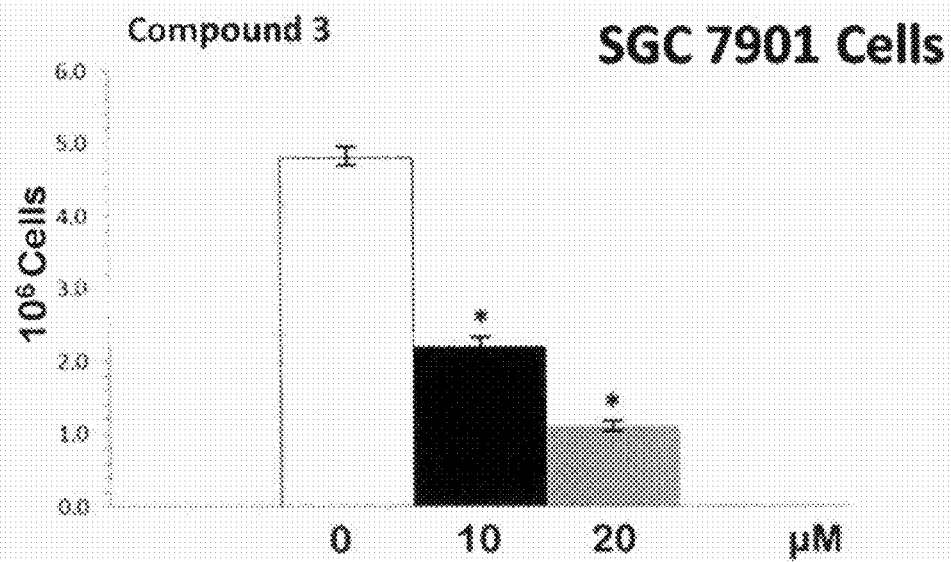
FIG. 10B is a bar graph showing the concentration-dependent antiproliferative effect of complex 3 on SGC7901 cells for 24 h.

Cell growth inhibition also depends on concentration of the drug. So, concentration dependent cell growth inhibition studies were made of gold(III) complexes 1-3 against human prostate PC3 and gastric SGC7901 cancer cells by using 10 μM and 20 μM concentrations. The results were according to the expectation that the cell inhibition was augmented with the increase in concentration of the complexes 1, 2 and 3 as shown in FIGS. 8 to 10 respectively. It is generally observed from FIGS. 8 to 10 that concentration dependent antiproliferative effects of complexes 1, 2 and 3 on PC3 cancer cells are superior to those on SGC7901 cancer cells. In the concentration dependent cell growth inhibition study at two concentrations (10 μM and 20 μM), complex 1 showed much better cell inhibition against PC3 cancer cell line than complexes 3 and 2 as shown in FIGS. 8 to 10. Gold(III) complexes 2 and 3 demonstrated a comparable cell inhibition; against both PC3 and SGC7901 cell lines as shown in FIGS. 9 and 10 respectively.

Figure 11A:
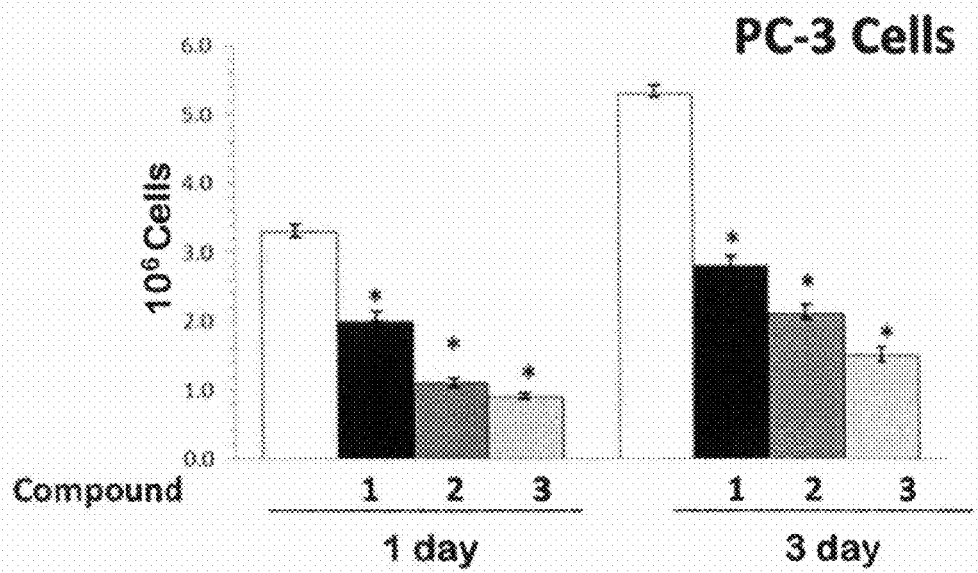
FIG. 11A is a bar graph comparing the untreated PC3 cells (white bar) and the time-dependent antiproliferative effect of 10 μM of complexes 1, 2, and 3 on PC3 cells for 24 and 72 h.
Figure 11B:
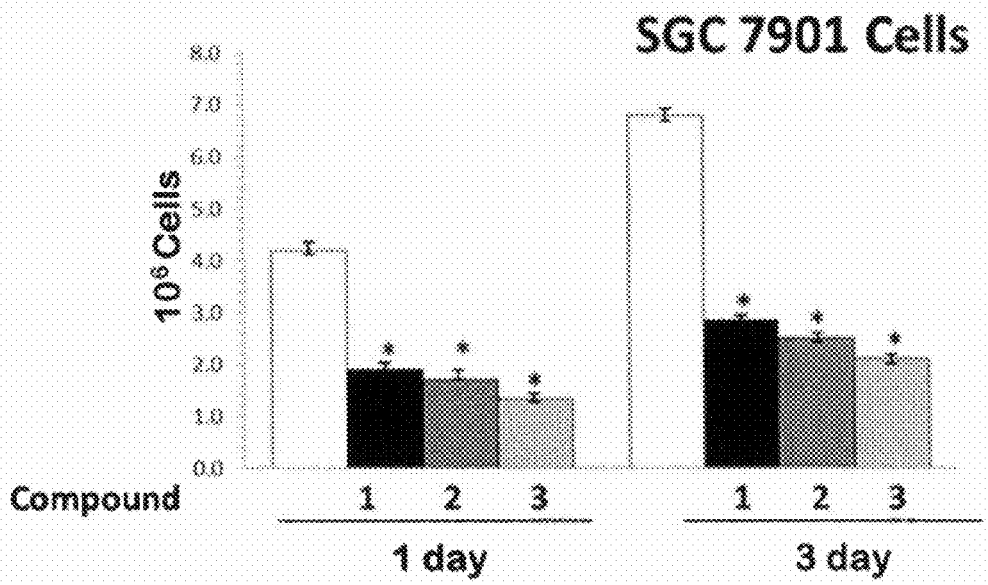
FIG. 11B is a bar graph comparing the untreated SGC7901 cells (white bar) and the time-dependent antiproliferative effect of 10 μM of complexes 1, 2, and 3 on SGC7901 cells for 24 and 72 h.

FIG. 11 illustrated the comparison of time dependent antiproliferative effects of 10 μM complexes 1, 2 and 3 on both PC3 and SGC7901 cancer cells for 24 h and 72 h. It has been observed that the order of time dependent antiproliferative effect is complex 3>complex 2>complex 1 for both PC3 and SGC7901 cancer cells. Such comparative study leads to conclusion that complex 3 is the most effective antiproliferative agent among mixed ligand based gold(III) complexes 1-3.

Even though the exact mechanisms on antiproliferation of [(DACH)Au(pn)]Cl$_3$ type complexes on PC3 and SGC 7901 cancer cell lines remains vague. The significantly diminished renal toxicity of [(DACH)Au(pn)]Cl$_3$ complexes could be attributed to their different antiproliferative mechanism of action and selective sparing of the proximal tubular epithelial cells [Ahmed A, Al Tamimi D M, Isab A A, Alkhawajah A M M, Shawarby M A (2012) PLoS ONE 7:e51889—incorporated herein by reference in its entirety].

Most gold(III) compounds display reduced affinity for DNA and it seems reasonable that DNA is neither the primary nor the exclusive target for most gold(III) complexes. Recent studies have proposed a different mode of action for these compounds, in most of the cases, induce apoptosis was the mode of cell death [Vivek S, Kyoungweon P, Mohan S (2009) Mater. Sci. Eng. R. 65:1-38; Niemeyer C M (2001) Angew. Chem. Intl. Ed. 40:4128-4158; Pellegrino T, Kudera S, Liedl T, Javier A M, Manna L, Parak W J (2005) Small 1:48-63—each incorporated herein by reference in its entirety]. Their mechanism although not precisely delineated. However, the mechanisms associated with the inhibitory effects of complexes 1-3 on the proliferation of rapidly dividing cancer cells may be comprised of a cumulative impact on the induction of cell cycle blockage, interruption of the cell mitotic cycle, apoptosis (programmed cell death) and necrosis (premature cell death) [Taatjes D J, Sobel B E, Budd R C (2008) Histochem. Cell. Biol. 129: 33-43; Takemura G, Minatoguchi M S, Fujiwara H (2013) Int. J. Cardio. 167:2373-2386; Hayashi R, Nakatsui K, Sugiyama D, Kitajima T, Oohara N, Sugiya M, Osada S, Kodama H (2014) J. Inorg. Biochem. 137:109-114; and Allen F H, Kennard O, Watson D G, Brammer L, Orpen A G (1987) J. Chem. Soc. Perkin Trans. II:S1-S19—each incorporated herein by reference in their entirety].

Human gastric SGC7901 cells and prostate PC3 cells were incubated with these compounds at fixed concentrations or with water as a control to assess the inhibitory effect on cell growth. The standard MTT assay has been used to assess the inhibitory effect on cell growth. The cell survival versus drug concentration is plotted. Cytotoxicity was evaluated in vitro with reference to the IC$_{50}$ value. The half maximal inhibitory concentration (IC$_{50}$) is a measure of the effectiveness of a compound to inhibit biological or biochemical functions. According to the FDA, IC$_{50}$ represents the concentration of a drug/compound/complex that is required for 50% inhibition in vitro. It is evaluated from the survival curves as the concentration needed for a 50% reduction of survival. IC$_{50}$ values are expressed in μM. The IC$_{50}$ values were calculated from dose-response curves obtained in replicate experiments, as shown in Table 12.

TABLE 12

In vitro cytotoxicity data of the complexes 1,2 and 3 after the exposure of 72 h towards human cancer SGC7901 and PC3 cell lines.

| | IC$_{50}$$^a$ (μM) | |
|---|---|---|
| Compounds | SGC7901 | PC3 |
| Cisplatin | 7.3 ± 0.5 | 1.1 ± 0.1 |
| 1 | 10.8 ± 0.2 | 9.5 ± 0.2 |
| 2 | 10.9 ± 0.1 | 10.2 ± 0.1 |
| 3 | 10.1 ± 0.1 | 9.1 ± 0.1 |

$^a$concentration of sample required to reduce the cell growth of tumor cell line by 50%

The in vitro cytotoxic effect of mixed ligand gold(III) diamine complexes against androgen-resistant prostate PC3 and human gastric SGC7901 cancer cells were studied using MTT assay. The in vitro cytotoxic activity depends on the exposure time and the concentration of complexes. For that reason, we used different concentrations and a 3-day exposure protocol to determine the IC$_{50}$ values for all three complexes. The in vitro cytotoxicity in terms of IC$_{50}$ values of cisplatin for PC3 and SGC7901 cells was included for a comparison.

The IC$_{50}$ data for the gold(III) complexes 1, 2 and 3 showed in vitro cytotoxicity in a wide range of 1.1-10.2 μM for PC3 cells, as given in Table 12. For PC3 cancer cells, the order of in vitro cytotoxicity in terms of IC$_{50}$ values is cisplatin (1.1 μM)>complex 3 (9.1 μM)>complex 1 (9.5 μM)>complex 2 (10.2 μM) as it is known that lower the IC$_{50}$ value, higher the in vitro cytotoxicity. All three complexes showed similar cytotoxic activities and they have lower potency vis-a-vis cisplatin. Complex 3 are reasonably better cytotoxic agent than complexes 1 and 2 for SGC7901 cancer cells.

The IC$_{50}$ data for the gold(III) complexes 1, 2 and 3 showed in vitro cytotoxicity in the range of 10.1-10.9 μM for SGC7901 cells, as given in Table 12. It can apparent from IC$_{50}$ data for SGC7901 cancer cells that complexes 1, 2 and 3 showed comparable in vitro cytotoxicity to cisplatin. Complexes 3 is reasonably better cytotoxic agent than complexes 1 and 2 for SGC7901 cancer cells, the order of in vitro cytotoxicity in terms of IC$_{50}$ values is cisplatin (7.3 μM)>complex 3 (10.1 μM)>complex 1 (10.8 μM)>complex 2 (10.9 μM). It is worth-mentioning that the in vitro cytotoxicity of the complexes 1-3 are fairly similar to cisplatin. There is no doubt that present study is helpful for further exploiting and defining the potential role of gold(III) complexes in combat against prostate and gastric cancers.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A gold(III) complex having Formula I:

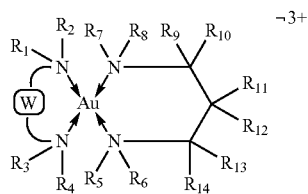

(I)

or a pharmaceutically acceptable salt, solvate, or prodrug thereof;
wherein W is selected from $W_1$ or $W_2$,

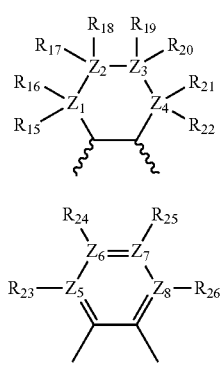

$R_1$-$R_8$ are each independently a hydrogen, an optionally substituted $C_1$-$C_8$ alkyl group, or an optionally substituted $C_6$-$C_8$ aryl group,
$R_9$-$R_{14}$ are each independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group,
$R_{15}$-$R_{26}$ are each independently a lone pair of electrons, a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group,
$Z_1$-$Z_4$ are each independently a carbon, an oxygen, a sulfur, or a nitrogen atom,
$Z_5$-$Z_8$ are each independently a carbon, or a nitrogen atom.

2. The gold(III) complex of claim 1, which has a formula selected from the group consisting of Formula II, Formula III, and Formula IV:

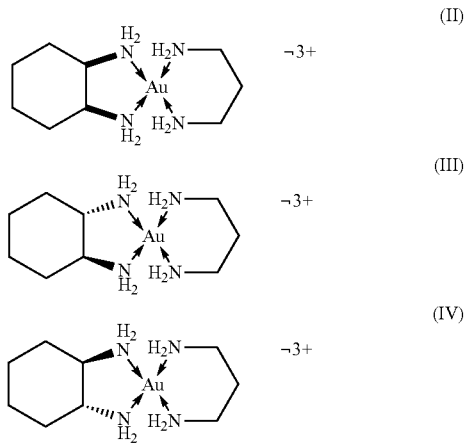

3. The gold(III) complex of claim 1, wherein the pharmaceutically acceptable salt comprises one or more pharmaceutically acceptable anions selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

4. A composition, comprising:
the gold(III) complex of claim 1 or a pharmaceutically acceptable salt, solvate or prodrug thereof; and
one or more pharmaceutically acceptable carriers.

5. The composition of claim 4, further comprising one or more other active pharmaceutical agents.

6. The composition of claim 4, comprising 50-99.9 wt % of the gold(III) complex relative to the total weight of the composition.

7. The composition of claim 4, wherein the composition is in solid, semi-solid or liquid dosage forms.

8. The composition of claim 4, wherein the composition is formulated for one or more modes of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

9. A method for treating one or more types of cancer in a mammalian subject in need thereof, comprising administering a therapeutically effective amount of the composition of claim 4 to the mammalian subject; wherein the one or more types of cancer are prostate cancer and/or gastrointestinal cancer.

10. The method of claim 9, wherein the gold(III) complex or a pharmaceutically acceptable salt, solvate or prodrug thereof, is administered in a dose of 0.05 mg/kg to 200 mg/kg based on the weight of the mammalian subject.

11. The method of claim 9, wherein the one or more types of cancer is resistant to cisplatin.

12. The method of claim 9, wherein the mammalian subject has a renal disease.

13. A method for inhibiting proliferation of cancer cells, comprising contacting the cancer cells with the gold(III)

complex of claim 1 or a pharmaceutically acceptable salt, solvate or prodrug thereof; wherein the cancer cells are prostate cancer cells and/or gastrointestinal cancer cells.

14. The method of claim 13, wherein the cancer cells are human cells.

15. The method of claim 13, wherein the prostate cancer cells are PC3 cells, and the gastrointestinal cancer cells are SGC7901 cells.

16. The method of claim 15, wherein the gold(III) complex exhibits an $IC_{50}$ of 1-20 μM for inhibiting the proliferation of the cancer cells.

* * * * *